(12) United States Patent
Park et al.

(10) Patent No.: US 9,299,935 B2
(45) Date of Patent: Mar. 29, 2016

(54) NITROGEN-CONTAINING HETEROCYCLIC COMPOUNDS AND ORGANIC ELECTRONIC DEVICE COMPRISING THE SAME

(71) Applicant: LG Chem, Ltd., Seoul (KR)

(72) Inventors: Tae Yoon Park, Daejeon (KR); Minseung Chun, Daejeon (KR); Sung Kil Hong, Daejeon (KR); Dong Hoon Lee, Daejeon (KR); Dongheon Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/239,297

(22) PCT Filed: Jun. 18, 2013

(86) PCT No.: PCT/KR2013/005340
§ 371 (c)(1),
(2) Date: Feb. 18, 2014

(87) PCT Pub. No.: WO2013/191428
PCT Pub. Date: Dec. 27, 2013

(65) Prior Publication Data
US 2014/0174538 A1    Jun. 26, 2014

(30) Foreign Application Priority Data

Jun. 18, 2012  (KR) .................. 10-2012-0064915
Apr. 22, 2013  (KR) .................. 10-2013-0044487

(51) Int. Cl.
*H01L 51/00*      (2006.01)
*C07D 471/04*    (2006.01)
*C09K 11/06*     (2006.01)
(Continued)

(52) U.S. Cl.
CPC .......... *H01L 51/0052* (2013.01); *C07D 471/04* (2013.01); *C09K 11/06* (2013.01); *H01L 51/0067* (2013.01); *H01L 51/0072* (2013.01); *H05B 33/14* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0054* (2013.01); *H01L 51/0058* (2013.01); *H01L 51/0073* (2013.01);
(Continued)

(58) Field of Classification Search
None
See application file for complete search history.

(56) References Cited

U.S. PATENT DOCUMENTS

| 6,229,012 | B1 | 5/2001 | Hu et al. |
| 7,014,925 | B2 | 3/2006 | Thoms |

(Continued)

FOREIGN PATENT DOCUMENTS

| CN | 101001935 A | 7/2007 |
| CN | 101010409 A | 8/2007 |

(Continued)

OTHER PUBLICATIONS

Machine translation of KR 10-2012-0015883. (Original provided by applicant.).*

(Continued)

*Primary Examiner* — Ling Choi
*Assistant Examiner* — Catherine S Branch
(74) *Attorney, Agent, or Firm* — Dentons US LLP

(57) ABSTRACT

The present disclosure provides a nitrogen-containing heterocyclic compound and an organic electronic device comprising the same.

16 Claims, 9 Drawing Sheets

(51) Int. Cl.
*H05B 33/14* (2006.01)
*H01L 51/50* (2006.01)

(52) U.S. Cl.
CPC ......... *H01L 51/0074* (2013.01); *H01L 51/0085* (2013.01); *H01L 51/5012* (2013.01)

(56) References Cited

U.S. PATENT DOCUMENTS

| | | |
|---|---|---|
| 2004/0219386 A1 | 11/2004 | Thoms |
| 2006/0060239 A1 | 3/2006 | Peumans et al. |
| 2007/0247059 A1 | 10/2007 | Cho et al. |
| 2008/0093980 A1 | 4/2008 | Stoessel et al. |
| 2011/0278549 A1 | 11/2011 | Kim et al. |

FOREIGN PATENT DOCUMENTS

| | | |
|---|---|---|
| CN | 101400757 A | 4/2009 |
| JP | 2008-510800 A | 4/2008 |
| JP | 2009-184987 | 8/2009 |
| KR | 2010-0112903 A | 10/2010 |
| KR | 10-2012-0015883 A | 2/2012 |
| KR | 2012-0015883 A | 2/2012 |
| WO | 2006/080640 A1 | 8/2006 |
| WO | WO 2006080640 A1 * | 8/2006 |
| WO | 2007105906 A1 | 9/2007 |
| WO | 2010/056070 A2 | 5/2010 |
| WO | 2011059271 A2 | 5/2011 |

OTHER PUBLICATIONS

Zuoquan Jiang et al., "Multifunctional Fluorene-Based Oligomers with Novel Spiro-Annulated Triarylamine: Efficient, Stable Deep-Blue Electroluminescence, Good Hole Injection, and Transporting Materials with Very High Tg", Adv. Funct. Mater. 2009, 19, 3987-3995.

* cited by examiner

NITROGEN-CONTAINING HETEROCYCLIC COMPOUNDS AND ORGANIC ELECTRONIC DEVICE COMPRISING THE SAME This application is a 35 USC §371 National Stage entry of International Application No. PCT/KR2013/005340, filed on Jun. 18, 2013, which claims priority of Korean Application No. 10-2012-0064915, filed on Jun. 18, 2012, and Korean Application No. 10-2013-0044487, filed on Apr. 22, 2013, all of which are hereby incorporated by reference in their entirety.

TECHNICAL FIELD

The present disclosure relates to a novel nitrogen-containing heterocyclic compound and to an organic electronic device comprising the same.

BACKGROUND ART

As used herein, the term "organic electronic device" refers to a device that requires the exchange of an electronic charge between an electrode and an organic material using holes and/or electrons. Organic electronic devices can be largely classified according to operational principle into the following two types. One type is an electronic device having a configuration in which an exciton is formed in an organic material layer by the entry of photons into the device from an external light source, and is then separated into an electron and a hole, which are transferred to different electrodes to create a current source (voltage source), and the other type is an electric device having a configuration in which a voltage or current is applied to two or more electrodes to inject a hole and/or an electron into an organic semiconductor positioned at the interface between the electrodes, and the device is operated using the injected electron and hole.

Examples of the organic electronic device include an organic light-emitting device, an organic solar cell, an organic photo-conductor (OPC), an organic transistor and the like, all of which require a hole-injecting or hole-transporting material, an electron-injecting or electron-transporting material or a light emitting material to drive the device. Hereinafter, the organic light-emitting device will be mainly and specifically described, but in the above-mentioned organic electronic devices, the hole-injecting material, hole-transporting material, electron-injecting material, electron-transporting material, and light-emitting material function according to a similar principle.

In general, the term "organic light-emitting phenomenon" refers to a phenomenon in which electrical energy is converted to light energy using an organic material. The organic light-emitting device that uses the organic light-emitting phenomenon usually has a structure comprising an anode, a cathode and an organic material layer interposed therebetween. Herein, the organic layer often has a multilayer structure consisting of a plurality of layers made of different materials in order to increase the efficiency and stability of the organic light-emitting device. For example, the organic material layer may consist of a hole-injecting layer, a hole-transporting layer, a light-emitting layer, an electron-transporting layer, an electron-injecting layer and the like. In the organic-light emitting device having this structure, when a voltage is applied between two electrodes, holes from the anode and electrons from the cathode are injected into the organic material layer, and the injected holes and electrons combine with each other to form excitons. When the excitons subsequently drop to the ground state, light is emitted. Such organic light-emitting devices are known to have characteristics, including self-luminescence, high brightness, high efficiency, low driving voltage, wide viewing angle, high contrast and high-speed response properties.

Materials that are used for organic material layers in organic light-emitting devices can be divided, according to function, into light-emitting materials and charge-transporting materials, for example, a hole-injecting material, a hole-transporting material, an electron-transporting material, an electron-injecting material and the like. Further, the light-emitting materials can be divided, according to the emitted color, into blue-, green- and red-emitting materials, and additionally into yellow- and orange-emitting materials, which are required in order to realize more natural colors. Meanwhile, when a single material is used as a light-emitting material, the peak emission wavelength is shifted to a longer wavelength by intermolecular interaction, and the color purity or the efficiency of the device decreases due to the emission attenuation. Thus, in order to increase the color purity and increase the light emission efficiency through energy transfer, a host/dopant system may be used as the light-emitting material.

In order for the organic light-emitting device to sufficiently exhibit the above-described excellent characteristics, materials constituting the organic layers in the device, for example, a hole-injecting material, a hole-transporting material, a light-emitting material, an electron-transporting material, an electron-injecting material and the like, should be supported using stable and efficient materials. However, the development of stable and efficient organic layer materials for organic light-emitting devices is still insufficient. Therefore, the development of novel materials for organic light-emitting devices has been continuously demanded, and the development of novel materials for other organic electronic devices as described above has also been demanded.

PRIOR ART DOCUMENTS

Korean Patent Laid-Open Publication No. 10-2006-0051606

DISCLOSURE

Technical Problem

The present inventors have found a nitrogen-containing heterocyclic compound having a novel structure. The present inventors have also found that an organic material layer of an organic electronic device comprising the novel nitrogen-containing heterocyclic compound can be formed.

Therefore, it is an object of the present disclosure to provide a nitrogen-containing heterocyclic compound and an organic electronic device comprising the same.

Technical Solution

The present disclosure provides a nitrogen-containing heterocyclic compound represented by the following formula 1:

Formula 1

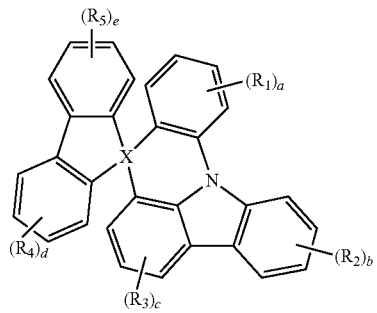

wherein

X is C or Si;

one or more of $R_1$ to $R_5$ are each independently represented by -L-A, wherein L is a direct bond or a divalent group containing one or more selected from the group consisting of a substituted or unsubstituted aromatic ring group and a substituted or unsubstituted heterocyclic group, and A is selected from the group consisting of a substituted or unsubstituted terphenyl group, a substituted or unsubstituted triphenylene group, a substituted or unsubstituted phenanthrene group, a substituted or unsubstituted phenanthroline group, a substituted or unsubstituted fluoranthene group, a substituted or unsubstituted fluorene group, a substituted or unsubstituted quinazoline group, a substituted or unsubstituted benzimidazole group, a substituted or unsubstituted dibenzothiophene group, and a substituted or unsubstituted dibenzofuran group; the remainder of $R_1$ to $R_5$ are selected from the group consisting of hydrogen, deuterium, a halogen group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorene group, a substituted or unsubstituted carbazole group, and a substituted or unsubstituted heterocyclic group containing at least one heteroatom selected from N, O and S;

a, b, d and e are each independently an integer ranging from 1 to 4; and c is an integer ranging from 1 to 3.

An embodiment of the present disclosure also provides an organic electronic device comprising a first electrode, a second electrode opposite the first electrode, and one or more organic material layers interposed between the first electrode and the second electrode, wherein at least one of the organic material layers comprises the above nitrogen-containing heterocyclic compound.

An embodiment of the present disclosure also provides a method for fabricating an organic electronic device, the method comprising the steps of: providing a substrate; forming a first electrode on the substrate; forming, over the first electrode, an organic material layer comprising the above nitrogen-containing heterocyclic compound; and forming a second electrode over the organic material layer.

Advantageous Effects

According to an embodiment of the present disclosure, the nitrogen-containing heterocyclic compound may be used as a material for an organic material layer in organic electronic devices, including organic light-emitting devices.

According to an embodiment of the present disclosure, the nitrogen-containing heterocyclic compound has excellent thermal stability.

According to an embodiment of the present disclosure, the nitrogen-containing heterocyclic compound has a deep HOMO level.

According to an embodiment of the present disclosure, the nitrogen-containing heterocyclic compound has a high triplet state.

According to an embodiment of the present disclosure, the nitrogen-containing heterocyclic compound has high hole stability.

According to an embodiment of the present disclosure, the nitrogen-containing heterocyclic compound may be used in a pure or impure state in organic electronic devices, including organic light-emitting devices.

According to an embodiment of the present disclosure, the nitrogen-containing heterocyclic compound shows high efficiency.

According to an embodiment of the present disclosure, the nitrogen-containing heterocyclic compound shows excellent characteristics in terms of driving voltage.

According to an embodiment of the present disclosure, an organic electronic device comprising the nitrogen-containing heterocyclic compound has a long lifespan.

According to an embodiment of the present disclosure, an organic electronic device comprising the nitrogen-containing heterocyclic compound can have improved photoefficiency.

According to an embodiment of the present disclosure, an organic electronic device comprising the nitrogen-containing heterocyclic compound can have an increased lifespan.

BEST MODE

Figure 1:
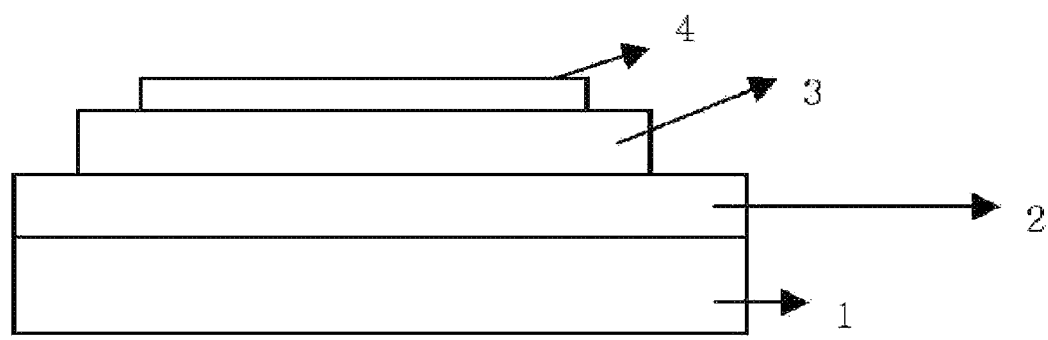
FIG. 1 shows an example of an organic light-emitting device comprising a substrate 1, an anode 2, a light-emitting layer 3 and a cathode 4.
Figure 2:
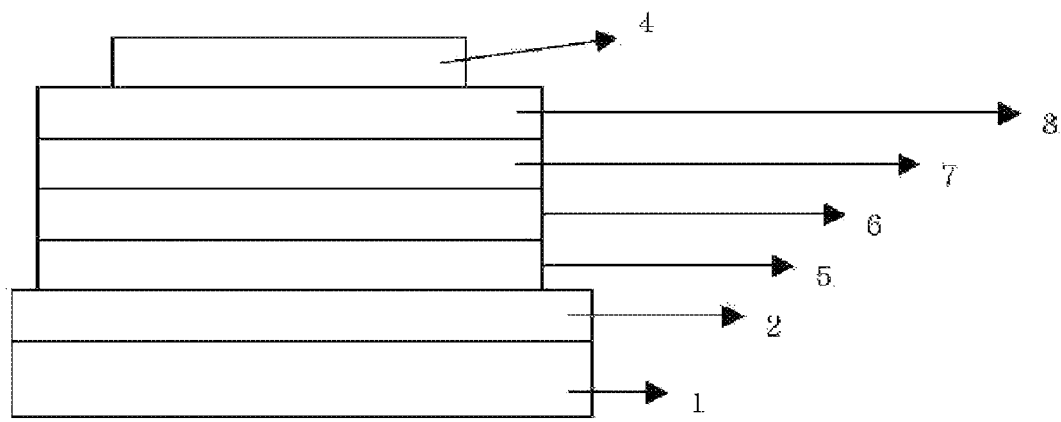
FIG. 2 shows an example of an organic light-emitting device comprising a substrate 1, an anode 2, a hole-injecting layer 5, a hole-transporting layer 6, a light-emitting layer 7, an electron-transporting layer 8 and a cathode 4.

Hereinafter, the present disclosure will be described in detail.

An embodiment of the present disclosure provides the nitrogen-containing heterocyclic compound represented by formula 1 above.

In the present disclosure,

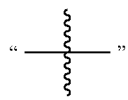

means a portion linked to another substituent group or portion.

In the present disclosure, the term "substituted or unsubstituted" means unsubstituted or substituted with one or more substituents selected from the group consisting of a halogen group, a nitrile group, a nitro group, a hydroxyl group, an alkyl group, a cycloalkyl group, an alkenyl group, an alkoxy group, an aryloxy group, a thiol group, an alkylthio group, an allylthio group, a sulfoxy group, an alkylsulfoxy group, an arylsulfoxy group, a silyl group, a boron group, an arylamine group, an aralkylamine group, an alkylamine group, an aryl group, a fluorene group, a carbazole group, an arylalkyl group, an arylalkenyl group, a heterocyclic group and an acetylene group.

In the present disclosure, the heterocyclic group is a heterocyclic group containing at least one heteroatom selected from O, N and S, and the number of carbon atoms thereof is preferably 2 to 60, but is not specifically limited thereto. Examples of the heterocyclic group include, but are not limited to, thiophene, furan, pyrrole, imidazole, thiazole, oxazole, oxadiazole, triazole, pyridyl, bipyridyl, triazine, acridyl, pyridazine, quinolinyl, isoquinolinyl, indole, carbazole, benzoxazole, benzimidazole, benzothiazole, benzocarbazole, benzothiophene, dibenzothiophene, benzofuranyl and dibenzofuran groups.

In the present disclosure, examples of the halogen group include fluorine, chlorine, bromine and iodine.

In the present disclosure, the alkyl group may be linear, branched or cyclic, and the number of carbon atoms thereof is preferably 1 to 25, but is not specifically limited thereto. Specific examples of the alkyl group include, but are not limited to, methyl, ethyl, n-propyl, iso-propyl, n-butyl, sec-butyl, t-butyl, n-pentyl, iso-pentyl, neo-pentyl, n-hexyl, cyclopropyl, cyclobutyl, cyclopentyl and cyclohexyl groups.

In the present disclosure, the cycloalkyl group preferably has 3 to 60 carbon atoms, but is not specifically limited thereto. Particularly, it is preferably a cyclopentyl or cyclohexyl group.

In the present disclosure, the alkenyl group may be linear or branched and is preferably a $C_2$-$C_{40}$ alkenyl group. Specifically, it is preferably an aryl-substituted alkenyl group such as a stylbenzyl or styrenyl group, but is not limited thereto.

In the present disclosure, the alkoxy group may be linear, branched or cyclic. The number of carbon atom of the alkoxy group is preferably 1 to 25, but is not specifically limited thereto. Specific examples of the alkoxy group include, but are not limited to, methoxy, ethoxy, n-propyloxy, iso-propyloxy, n-butyloxy and cyclopentyloxy groups.

In the present disclosure, the aryl group may be a monocyclic or polycyclic aryl group, which may be substituted with a $C_1$-$C_{25}$ alkyl group or a $C_1$-$C_{25}$ alkoxy group. In addition, the aryl group in the present disclosure may mean an aromatic ring. When the aryl group is a monocyclic aryl group, the number of carbon atoms thereof is preferably 6 to 25, but is not specifically limited thereto. Specific examples of the monocyclic aryl group include, but are not limited to, phenyl, biphenyl, terphenyl and stylbenzyl groups.

When the aryl group is a polycyclic aryl group, the number of carbon atoms thereof is preferably 10 to 24, but is not specifically limited thereto. Specific examples of the polycyclic aryl group include, but are not limited to, naphthyl, anthranyl, phenanthryl, pyrenyl, perylenyl, chrysenyl and fluorenyl groups.

In the present disclosure, the fluorenyl group has a structure in which two cyclic organic compounds are linked to each other by one atom.

In the present disclosure, the fluorenyl groups include an open fluorenyl group having a structure in which one of two cyclic compounds linked to each other by one atom is broken. When the fluorenyl group is substituted, it may be

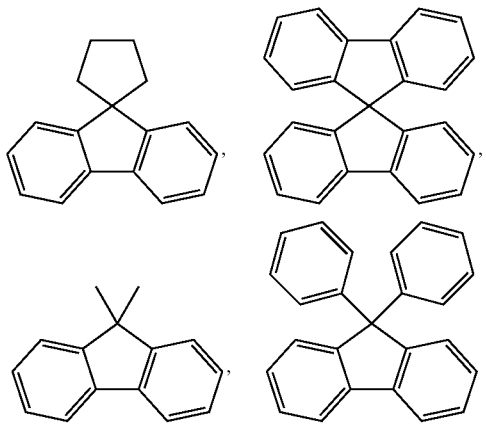

or the like, but is not limited thereto.

In the present disclosure, examples of the arylamine group include substituted or unsubstituted monocyclic diarylamine, substituted or unsubstituted polycyclic diarylamine, and substituted or unsubstituted monocyclic or polycyclic diarylamine groups.

According to an embodiment of the present disclosure, A in formula 1 may be a substituted or unsubstituted terphenyl group. Specifically, the substituted or unsubstituted terphenyl group may be represented by any one of the following formulas, and the carbon atom of the terphenyl group may be substituted or unsubstituted:

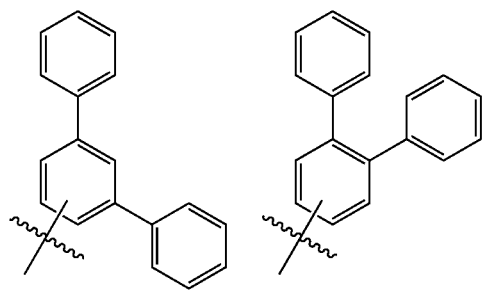

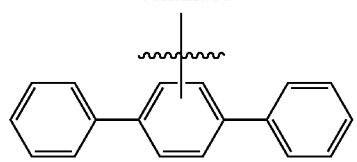

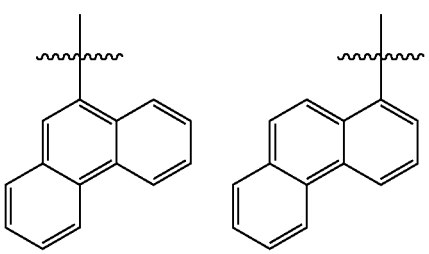

According to an embodiment of the present disclosure, A in formula 1 may be a substituted or unsubstituted phenanthroline group. Specifically, the substituted or unsubstituted phenanthroline group may be represented by any one of the following formulas, and the carbon atom of the phenanthroline group may be substituted or unsubstituted:

According to an embodiment of the present disclosure, A in formula 1 may be a substituted or unsubstituted triphenylene group. Specifically, the substituted or unsubstituted triphenylene group may be represented by any one of the following formulas, and the carbon atom of the triphenylene group may be substituted or unsubstituted:

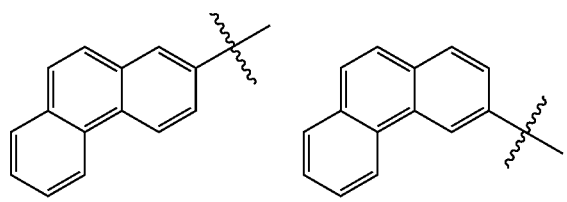

According to an embodiment of the present disclosure, A in formula 1 may be a substituted or unsubstituted phenanthrene group. Specifically, the substituted or unsubstituted phenanthrene group may be represented by any one of the following formulas, and the carbon atom of the phenanthrene group may be substituted or unsubstituted:

According to an embodiment of the present disclosure, A in formula 1 may be a substituted or unsubstituted fluoranthene group. Specifically, the substituted or unsubstituted fluoranthene group may be represented by any one of the following formulas, and the carbon atom of the fluoranthene group may be substituted or unsubstituted:

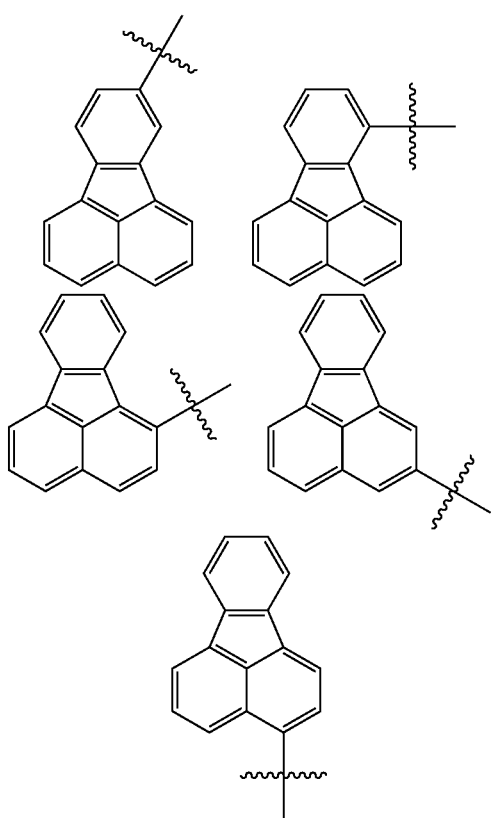

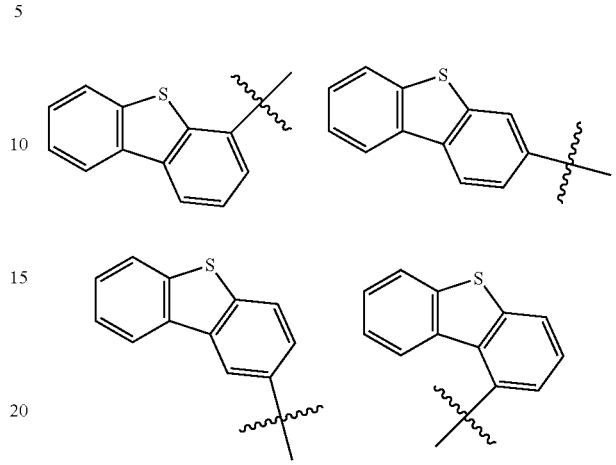

zothiophene group. Specifically, the substituted or unsubstituted dibenzothiophene group may be represented by any one of the following formulas, and the carbon atom of the dibenzothiophene group may be substituted or unsubstituted:

According to an embodiment of the present disclosure, A in formula 1 may be a substituted or unsubstituted fluorene group. Specifically, the substituted or unsubstituted fluorene group may be represented by any one of the following formulas, and the carbon atom of the fluorene group may be substituted or unsubstituted:

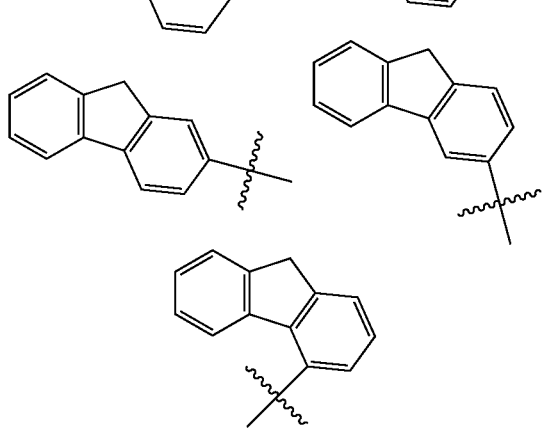

According to an embodiment of the present disclosure, A in formula 1 may be a substituted or unsubstituted diben- According to an embodiment of the present disclosure, A in formula 1 may be a substituted or unsubstituted dibenzofuran group. Specifically, the substituted or unsubstituted dibenzofuran group may be represented by any one of the following formulas, and the carbon atom of the dibenzofuran group may be substituted or unsubstituted:

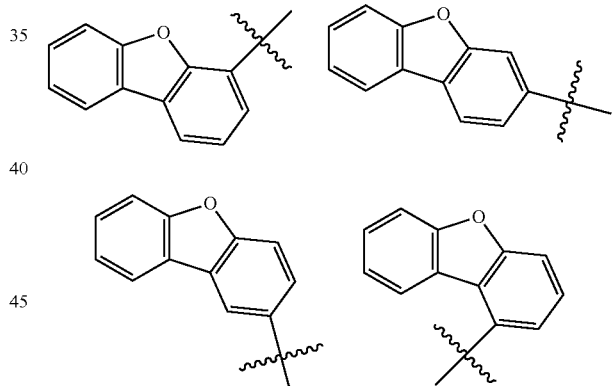

According to an embodiment of the present disclosure, A in formula 1 may be a substituted or unsubstituted quinazoline group. Specifically, the substituted or unsubstituted quinazoline group may be represented by any one of the following formulas, and the carbon atom of the quinazoline group may be substituted or unsubstituted:

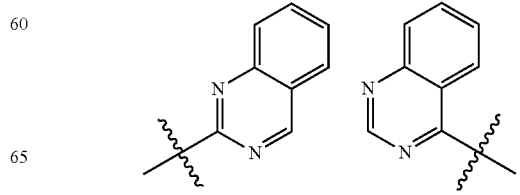

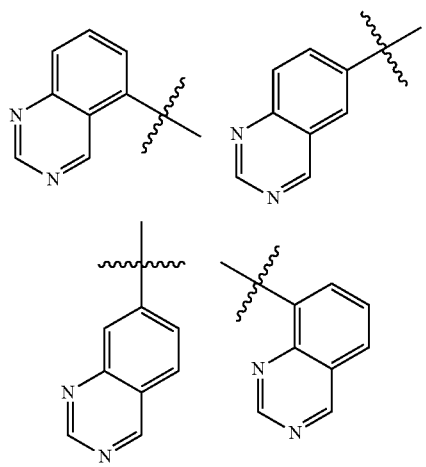

According to an embodiment of the present disclosure, A in formula 1 may be a substituted or unsubstituted benzimidazole group. Specifically, the substituted or unsubstituted benzimidazole group may be represented by any one of the following formulas, and the carbon atom of the benzimidazole group may be substituted or unsubstituted:

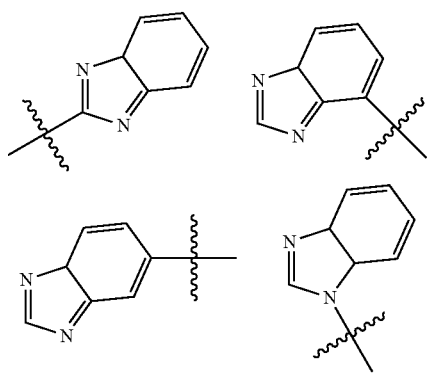

According to an embodiment of the present disclosure, L in the compound represented by formula 1 may be a substituted or unsubstituted phenylene group. Specifically, the substituted or unsubstituted phenylene group may be represented by any one of the following formulas, and the carbon atom of the phenylene group may be substituted or unsubstituted:

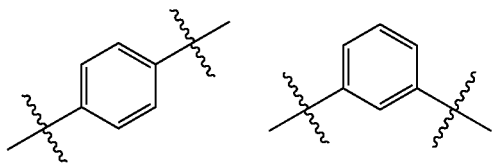 [SMILES: *c1ccc(*)cc1 ; *c1cccc(*)c1]

According to an embodiment of the present disclosure, L in the compound represented by formula 1 may be a substituted or unsubstituted biphenyl group. Specifically, the substituted or unsubstituted biphenyl group may be represented by any one of the following formulas, and the carbon atom of the biphenyl group may be substituted or unsubstituted:

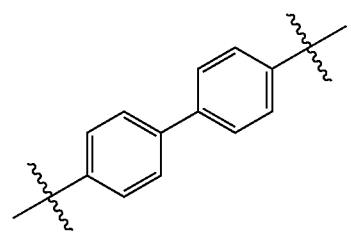

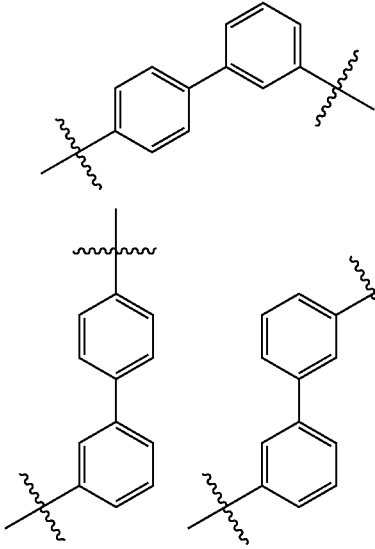

According to an embodiment of the present disclosure, L in the compound represented by formula 1 may be a substituted or unsubstituted naphthalene group. Specifically, the substituted or unsubstituted naphthalene group may be represented by any one of the following formulas, and the carbon atom of the naphthalene group may be substituted or unsubstituted:

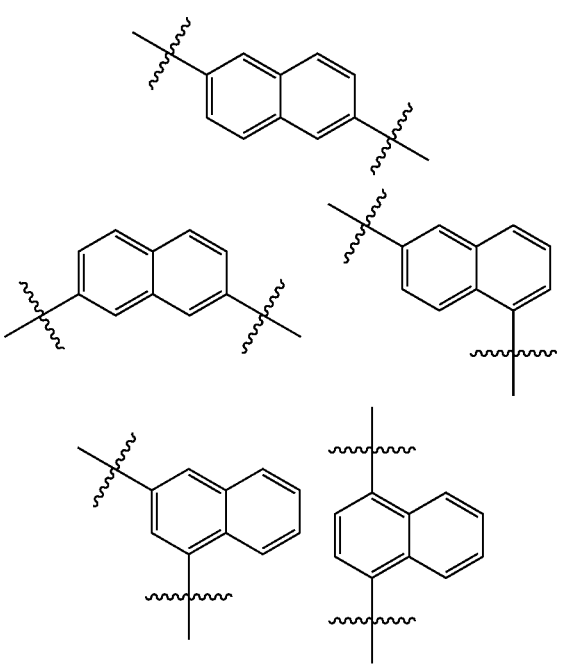

-continued

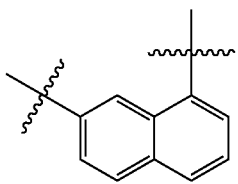

According to an embodiment of the present disclosure, L in the compound represented by formula 1 may be a substituted or unsubstituted anthracene group. Specifically, the substituted or unsubstituted anthracene group may be represented by any one of the following formulas, and the carbon atom of the anthracene group may be substituted or unsubstituted:

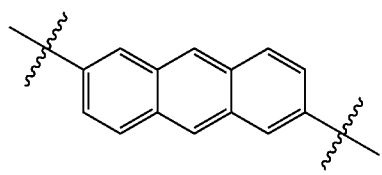

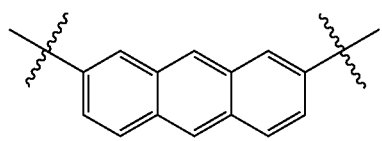

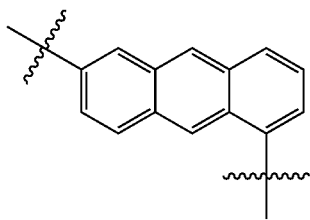

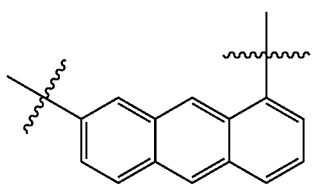

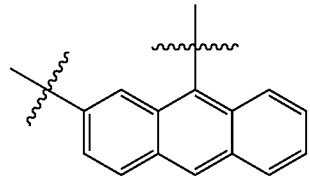

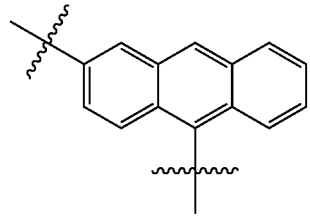

-continued

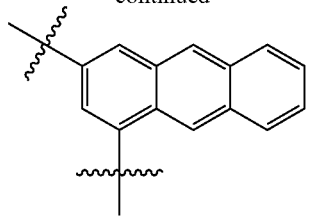

According to an embodiment of the present disclosure, L in the compound represented by formula 1 may be a direct bond.

According to an embodiment of the present disclosure, L in the compound represented by formula 1 may be a phenylene group, and A is a substituted or unsubstituted terphenyl group.

According to an embodiment of the present disclosure, L in the compound represented by formula 1 may be a phenylene group, and A is a substituted or unsubstituted triphenylene group.

According to an embodiment of the present disclosure, L in the compound represented by formula 1 may be a phenylene group, and A is a substituted or unsubstituted phenanthrene group.

According to an embodiment of the present disclosure, L in the compound represented by formula 1 may be a phenylene group, and A is a substituted or unsubstituted phenanthroline group.

According to an embodiment of the present disclosure, L in the compound represented by formula 1 may be a phenylene group, and A is a substituted or unsubstituted fluoranthene group.

According to an embodiment of the present disclosure, L in the compound represented by formula 1 may be a phenylene group, and A is a substituted or unsubstituted fluorene group.

According to an embodiment of the present disclosure, L in the compound represented by formula 1 may be a phenylene group, and A is a substituted or unsubstituted quinazoline group.

According to an embodiment of the present disclosure, L in the compound represented by formula 1 may be a phenylene group, and A is a substituted or unsubstituted benzimidazole group.

According to an embodiment of the present disclosure, L in the compound represented by formula 1 may be a phenylene group, and A is a substituted or unsubstituted dibenzothiophene group.

According to an embodiment of the present disclosure, L in the compound represented by formula 1 may be a phenylene group, and A is a substituted or unsubstituted dibenzofuran group.

According to an embodiment of the present disclosure, L in the compound represented by formula 1 may be a direct bond, and A is an alkyl-substituted benzimidazole group.

According to an embodiment of the present disclosure, L in the compound represented by formula 1 may be a direct bond, and A is an alkyl-substituted quinazoline group.

According to an embodiment of the present disclosure, L in the compound represented by formula 1 may be a phenylene group, and A is an alkyl-substituted benzimidazole group.

According to an embodiment of the present disclosure, L in the compound represented by formula 1 may be a phenylene group, and A is a phenyl-substituted benzimidazole group.

According to an embodiment of the present disclosure, L in the compound represented by formula 1 may be a direct bond, and A is a phenyl-substituted quinazoline group.

According to an embodiment of the present disclosure, L in the compound represented by formula 1 may be a direct bond, and A is a biphenyl-substituted quinazoline group.

According to an embodiment of the present disclosure, -L-A in formula 1 may be any one substituent of the following substituents 1-1 to 1-16. In addition, according to an embodiment of the present disclosure, the carbon atom of the following substituents may be substituted or unsubstituted.

Substituent 1-1
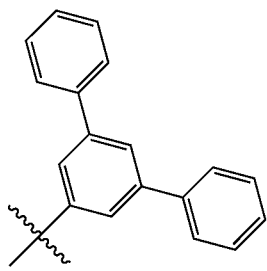

Substituent 1-2
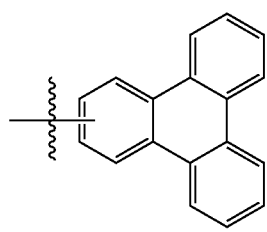

Substituent 1-3
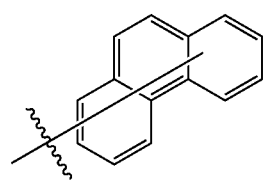

Substituent 1-4
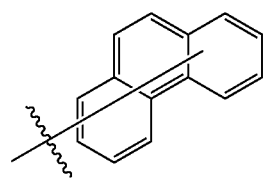

Substituent 1-5
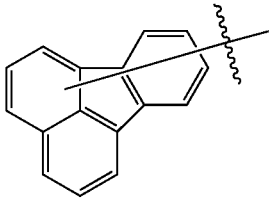

Substituent 1-6
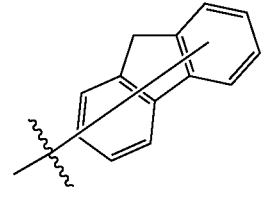

Substituent 1-7
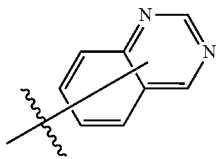

Substituent 1-8
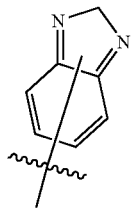

Substituent 1-9
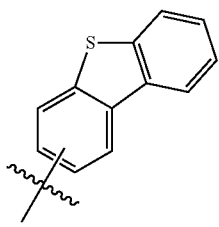

Substituent 1-10
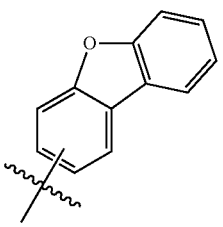

Substituent 1-11
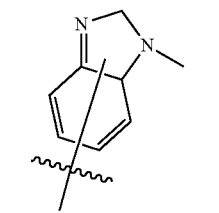

Substituent 1-12
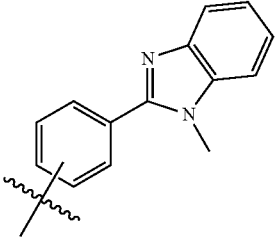

Substituent 1-13
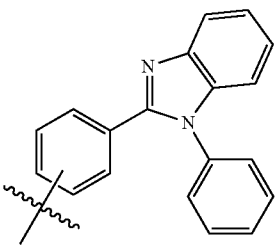

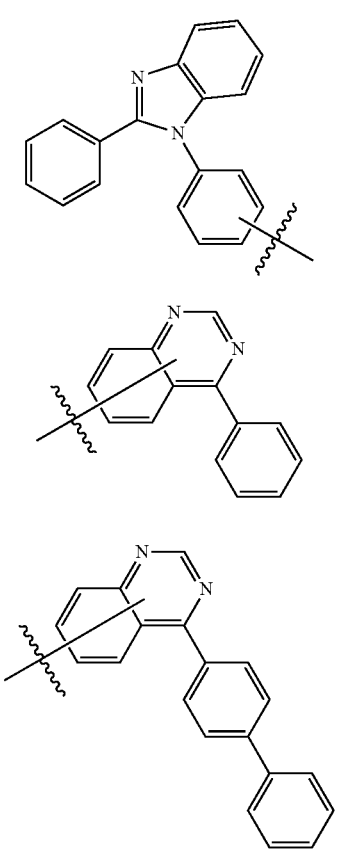

Substituent 1-14

Substituent 1-15

Substituent 1-16

According to an embodiment of the present disclosure, X in the compound represented by formula 1 may be carbon.

According to an embodiment of the present disclosure, one or two of a, b, c, d and e formula 1 may be 1.

According to an embodiment of the present disclosure, X in formula 1 is carbon, and $R_1$ is 4-phenylquinazoline group.

According to an embodiment of the present disclosure, X in formula 1 is carbon, and $R_1$ is 4-(biphenyl-4-yl) quinazoline group.

According to an embodiment of the present disclosure, X in formula 1 is carbon, and $R_1$ is 1-methyl-2-phenyl-1H-benzo[d]imidazole group.

According to an embodiment of the present disclosure, X in formula 1 is carbon, and $R_1$ is 1,2-diphenyl-1H-benzo[d]imidazole group.

According to an embodiment of the present disclosure, X in formula 1 is carbon, and $R_1$ is dibenzofuran group.

According to an embodiment of the present disclosure, X in formula 1 is carbon, and $R_1$ is dibenzothiophene group.

According to an embodiment of the present disclosure, X in formula 1 is carbon, and $R_1$ is terphenyl group.

According to an embodiment of the present disclosure, X in formula 1 is carbon, and $R_1$ is triphenylene group.

According to an embodiment of the present disclosure, X in formula 1 is carbon, and $R_1$ is phenanthrene group.

According to an embodiment of the present disclosure, X in formula 1 is carbon, and $R_1$ is 1,10-phenanthroline group.

According to an embodiment of the present disclosure, X in formula 1 is carbon, and $R_1$ is fluoranthene group.

According to an embodiment of the present disclosure, X in formula 1 is carbon, and $R_1$ is fluorene group.

According to an embodiment of the present disclosure, X in formula 1 is carbon, and $R_2$ is dibenzofuran group.

According to an embodiment of the present disclosure, X in formula 1 is carbon, and $R_2$ is dibenzothiophene group.

According to an embodiment of the present disclosure, X in formula 1 is carbon, and $R_2$ is terphenyl group.

According to an embodiment of the present disclosure, X in formula 1 is carbon, and $R_2$ is triphenylene group.

According to an embodiment of the present disclosure, X in formula 1 is carbon, and $R_2$ is phenanthrene group.

According to an embodiment of the present disclosure, X in formula 1 is carbon, and $R_2$ is 1,10-phenanthroline group.

According to an embodiment of the present disclosure, X in formula 1 is carbon, and $R_2$ is fluoranthene group.

According to an embodiment of the present disclosure, X in formula 1 is carbon, and $R_2$ is fluorene group.

According to an embodiment of the present disclosure, X in formula 1 is carbon, and $R_3$ is dibenzofuran group.

According to an embodiment of the present disclosure, X in formula 1 is carbon, and $R_3$ is dibenzothiophene group.

According to an embodiment of the present disclosure, X in formula 1 is carbon, and $R_3$ is terphenyl group.

According to an embodiment of the present disclosure, X in formula 1 is carbon, and $R_3$ is triphenylene group.

According to an embodiment of the present disclosure, X in formula 1 is carbon, and $R_3$ is phenanthrene group.

According to an embodiment of the present disclosure, X in formula 1 is carbon, and $R_3$ is 1,10-phenanthroline group.

According to an embodiment of the present disclosure, X in formula 1 is carbon, and $R_3$ is fluoranthene group.

According to an embodiment of the present disclosure, X in formula 1 is carbon, and $R_3$ is fluorene group.

According to an embodiment of the present disclosure, X in formula 1 is carbon, and $R_4$ is dibenzofuran group.

According to an embodiment of the present disclosure, X in formula 1 is carbon, and $R_4$ is dibenzothiophene group.

According to an embodiment of the present disclosure, X in formula 1 is carbon, and $R_4$ is terphenyl group.

According to an embodiment of the present disclosure, X in formula 1 is carbon, and $R_4$ is triphenylene group.

According to an embodiment of the present disclosure, X in formula 1 is carbon, and $R_4$ is phenanthrene group.

According to an embodiment of the present disclosure, X in formula 1 is carbon, and $R_4$ is 1,10-phenanthroline group.

According to an embodiment of the present disclosure, X in formula 1 is carbon, and $R_4$ is fluoranthene group.

According to an embodiment of the present disclosure, X in formula 1 is carbon, and $R_4$ is fluorene group.

According to an embodiment of the present disclosure, X in formula 1 is carbon, and $R_5$ is 4-phenylquinazoline group.

According to an embodiment of the present disclosure, X in formula 1 is carbon, and $R_5$ is 4-(biphenyl-4-yl)quinazoline group.

According to an embodiment of the present disclosure, X in formula 1 is carbon, and $R_5$ is 1-methyl-2-phenyl-1H-benzo[d]imidazole group.

According to an embodiment of the present disclosure, X in formula 1 is carbon, and $R_5$ is 1,2-diphenyl-1H-benzo[d]imidazole group.

According to an embodiment of the present disclosure, X in formula 1 is carbon, and $R_5$ is dibenzofuran group.

According to an embodiment of the present disclosure, X in formula 1 is carbon, and $R_5$ is dibenzothiophene group.

According to an embodiment of the present disclosure, X in formula 1 is carbon, and $R_5$ is terphenyl group.

According to an embodiment of the present disclosure, X in formula 1 is carbon, and $R_5$ is triphenylene group.

According to an embodiment of the present disclosure, X in formula 1 is carbon, and $R_5$ is phenanthrene group.

According to an embodiment of the present disclosure, X in formula 1 is carbon, and $R_5$ is 1,10-phenanthroline group.

According to an embodiment of the present disclosure, X in formula 1 is carbon, and $R_5$ is fluoranthene group.

According to an embodiment of the present disclosure, X in formula 1 is carbon, and $R_5$ is fluorene group.

According to an embodiment of the present disclosure, X in formula 1 is carbon, and $R_2$ and $R_3$ are dibenzofuran group.

According to an embodiment of the present disclosure, X in formula 1 is carbon, and $R_2$ and $R_3$ are dibenzothiophene group.

According to an embodiment of the present disclosure, X in formula 1 is carbon, and $R_2$ and $R_3$ are terphenyl group.

According to an embodiment of the present disclosure, X in formula 1 is carbon, and $R_2$ and $R_3$ are triphenylene group.

According to an embodiment of the present disclosure, X in formula 1 is carbon, and $R_2$ and $R_3$ are phenanthrene group.

According to an embodiment of the present disclosure, X in formula 1 is carbon, and $R_2$ and $R_3$ are 1,10-phenanthroline group.

According to an embodiment of the present disclosure, X in formula 1 is carbon, and $R_2$ and $R_3$ are fluoranthene group.

According to an embodiment of the present disclosure, X in formula 1 is carbon, and $R_2$ and $R_3$ are fluorene group.

According to an embodiment of the present disclosure, X in formula 1 is carbon, $R_1$ is 4-phenylquinazoline group, and $R_2$ to $R_5$ are hydrogen.

According to an embodiment of the present disclosure, X in formula 1 is carbon, $R_1$ is 4-(biphenyl-4-yl)quinazoline group, and $R_2$ to $R_5$ are hydrogen.

According to an embodiment of the present disclosure, X in formula 1 is carbon, $R_1$ is 1-methyl-2-phenyl-1H-benzo[d]imidazole group, and $R_2$ to $R_5$ are hydrogen.

According to an embodiment of the present disclosure, X in formula 1 is carbon, $R_1$ is 1,2-diphenyl-1H-benzo[d]imidazole group, and $R_2$ to $R_5$ are hydrogen.

According to an embodiment of the present disclosure, X in formula 1 is carbon, $R_1$ is dibenzofuran group, and $R_2$ to $R_5$ are hydrogen.

According to an embodiment of the present disclosure, X in formula 1 is carbon, $R_1$ is dibenzothiophene group, and $R_2$ to $R_5$ are hydrogen.

According to an embodiment of the present disclosure, X in formula 1 is carbon, $R_1$ is terphenyl group, and $R_2$ to $R_5$ are hydrogen.

According to an embodiment of the present disclosure, X in formula 1 is carbon, $R_1$ is triphenylene group, and $R_2$ to $R_5$ are hydrogen.

According to an embodiment of the present disclosure, X in formula 1 is carbon, $R_1$ is phenanthrene group, and $R_2$ to $R_5$ are hydrogen.

According to an embodiment of the present disclosure, X in formula 1 is carbon, $R_1$ is 1,10-phenanthroline group, and $R_2$ to $R_5$ are hydrogen.

According to an embodiment of the present disclosure, X in formula 1 is carbon, $R_1$ is fluoranthene group, and $R_2$ to $R_5$ are hydrogen.

According to an embodiment of the present disclosure, X in formula 1 is carbon, $R_1$ is fluorene group, and $R_2$ to $R_5$ are hydrogen.

According to an embodiment of the present disclosure, X in formula 1 is carbon, $R_1$ is dibenzofuran group, and $R_2$ to $R_5$ are hydrogen.

According to an embodiment of the present disclosure, X in formula 1 is carbon, $R_1$ is dibenzothiophene group, and $R_2$ to $R_5$ are hydrogen.

According to an embodiment of the present disclosure, X in formula 1 is carbon, $R_1$ is terphenyl group, and $R_2$ to $R_5$ are hydrogen.

According to an embodiment of the present disclosure, X in formula 1 is carbon, $R_2$ is triphenylene group, and $R_1$ and $R_3$ to $R_5$ are hydrogen.

According to an embodiment of the present disclosure, X in formula 1 is carbon, $R_2$ is phenanthrene group, and $R_1$ and $R_3$ to $R_5$ are hydrogen.

According to an embodiment of the present disclosure, X in formula 1 is carbon, $R_2$ is 1,10-phenanthroline group, and $R_1$ and $R_3$ to $R_5$ are hydrogen.

According to an embodiment of the present disclosure, X in formula 1 is carbon, $R_2$ is fluoranthene group, and $R_1$ and $R_3$ to $R_5$ are hydrogen.

According to an embodiment of the present disclosure, X in formula 1 is carbon, $R_2$ is fluorene group, and $R_1$ and $R_3$ to $R_5$ are hydrogen.

According to an embodiment of the present disclosure, X in formula 1 is carbon, $R_3$ is dibenzofuran group, and $R_1$, $R_2$, $R_4$ and $R_5$ are hydrogen.

According to an embodiment of the present disclosure, X in formula 1 is carbon, $R_3$ is dibenzothiophene group, and $R_1$, $R_2$, $R_4$ and $R_5$ are hydrogen.

According to an embodiment of the present disclosure, X in formula 1 is carbon, $R_3$ is terphenyl group, and $R_1$, $R_2$, $R_4$ and $R_5$ are hydrogen.

According to an embodiment of the present disclosure, X in formula 1 is carbon, $R_3$ is triphenylene group, and $R_1$, $R_2$, $R_4$ and $R_5$ are hydrogen.

According to an embodiment of the present disclosure, X in formula 1 is carbon, $R_3$ is 1,10-phenanthroline group, and $R_1$, $R_2$, $R_4$ and $R_5$ are hydrogen.

According to an embodiment of the present disclosure, X in formula 1 is carbon, $R_3$ is fluoranthene group, and $R_1$, $R_2$, $R_4$ and $R_5$ are hydrogen.

According to an embodiment of the present disclosure, X in formula 1 is carbon, $R_3$ is fluorene group, and $R_1$, $R_2$, $R_4$ and $R_5$ are hydrogen.

According to an embodiment of the present disclosure, X in formula 1 is carbon, $R_4$ is dibenzofuran group, and $R_1$ to $R_3$ and $R_5$ are hydrogen.

According to an embodiment of the present disclosure, X in formula 1 is carbon, $R_4$ is dibenzothiophene group, and $R_1$ to $R_3$ and $R_5$ are hydrogen.

According to an embodiment of the present disclosure, X in formula 1 is carbon, $R_4$ is terphenyl group, and $R_1$ to $R_3$ and $R_5$ are hydrogen.

According to an embodiment of the present disclosure, X in formula 1 is carbon, $R_4$ is triphenylene group, and $R_1$ to $R_3$ and $R_5$ are hydrogen.

According to an embodiment of the present disclosure, X in formula 1 is carbon, $R_4$ is phenanthrene group, and $R_1$ to $R_3$ and $R_5$ are hydrogen.

According to an embodiment of the present disclosure, X in formula 1 is carbon, $R_4$ is 1,10-phenanthroline group, and $R_1$ to $R_3$ and $R_5$ are hydrogen.

According to an embodiment of the present disclosure, X in formula 1 is carbon, $R_4$ is fluoranthene group, and $R_1$ to $R_3$ and $R_5$ are hydrogen.

According to an embodiment of the present disclosure, X in formula 1 is carbon, $R_4$ is fluorene group, and $R_1$ to $R_3$ and $R_5$ are hydrogen.

According to an embodiment of the present disclosure, X in formula 1 is carbon, $R_5$ is 4-phenylquinazoline group, and $R_1$ to $R_4$ are hydrogen.

According to an embodiment of the present disclosure, X in formula 1 is carbon, $R_5$ is 4-(biphenyl-4-yl)quinazoline group, and $R_1$ to $R_4$ are hydrogen.

According to an embodiment of the present disclosure, X in formula 1 is carbon, $R_5$ is 2,4-di(naphthalen-1-yl)-1,3,5-triazine group, and $R_1$ to $R_4$ are hydrogen.

According to an embodiment of the present disclosure, X in formula 1 is carbon, $R_5$ is 1-methyl-2-phenyl-1H-benzo[d]imidazole group, and $R_1$ to $R_4$ are hydrogen.

According to an embodiment of the present disclosure, X in formula 1 is carbon, $R_5$ is 1,2-diphenyl-1H-benzo[d]imidazole group, and $R_1$ to $R_4$ are hydrogen.

According to an embodiment of the present disclosure, X in formula 1 is carbon, $R_5$ is dibenzofuran group, and $R_1$ to $R_4$ are hydrogen.

According to an embodiment of the present disclosure, X in formula 1 is carbon, $R_5$ is dibenzothiophene group, and $R_1$ to $R_4$ are hydrogen.

According to an embodiment of the present disclosure, X in formula 1 is carbon, $R_5$ is terphenyl group, and $R_1$ to $R_4$ are hydrogen.

According to an embodiment of the present disclosure, X in formula 1 is carbon, $R_5$ is triphenylene group, and $R_1$ to $R_4$ are hydrogen.

According to an embodiment of the present disclosure, X in formula 1 is carbon, $R_5$ is phenanthrene group, and $R_1$ to $R_4$ are hydrogen.

According to an embodiment of the present disclosure, X in formula 1 is carbon, $R_5$ is 1,10-phenanthroline group, and $R_1$ to $R_4$ are hydrogen.

According to an embodiment of the present disclosure, X in formula 1 is carbon, $R_5$ is fluoranthene group, and $R_1$ to $R_4$ are hydrogen.

According to an embodiment of the present disclosure, X in formula 1 is carbon, $R_5$ is fluorene group, and $R_1$ to $R_4$ are hydrogen.

According to an embodiment of the present disclosure, X in formula 1 is carbon, $R_2$ and $R_3$ are dibenzofuran group, and $R_1$, $R_4$ and $R_5$ are hydrogen.

According to an embodiment of the present disclosure, X in formula 1 is carbon, $R_2$ and $R_3$ are dibenzothiophene group, and $R_1$, $R_4$ and $R_5$ are hydrogen.

According to an embodiment of the present disclosure, X in formula 1 is carbon, $R_2$ and $R_3$ are terphenyl group, and $R_1$, $R_4$ and $R_5$ are hydrogen.

According to an embodiment of the present disclosure, X in formula 1 is carbon, $R_2$ and $R_3$ are phenanthrene group, and $R_1$, $R_4$ and $R_5$ are hydrogen.

According to an embodiment of the present disclosure, X in formula 1 is carbon, $R_2$ and $R_3$ are 1,10-phenanthroline group, and $R_1$, $R_4$ and $R_5$ are hydrogen.

According to an embodiment of the present disclosure, X in formula 1 is carbon, $R_2$ and $R_3$ are fluoranthene group, and $R_1$, $R_4$ and $R_5$ are hydrogen.

According to an embodiment of the present disclosure, X in formula 1 is carbon, $R_2$ and $R_3$ are fluorene group, and $R_1$, $R_4$ and $R_5$ are hydrogen.

According to an embodiment of the present disclosure, specific examples of the compound represented by formula 1 include, but are not limited to, compounds represented by the following formulas 2-1 to 2-78.

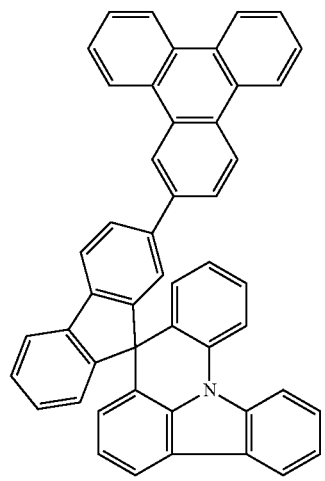

Formula 2-1

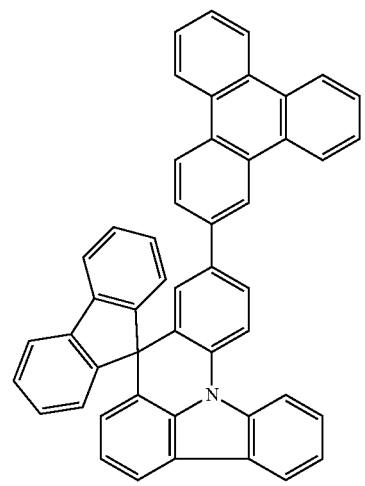

Formula 2-2

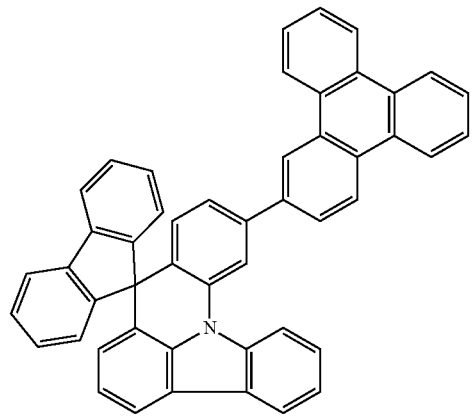

Formula 2-3

-continued
Formula 2-4
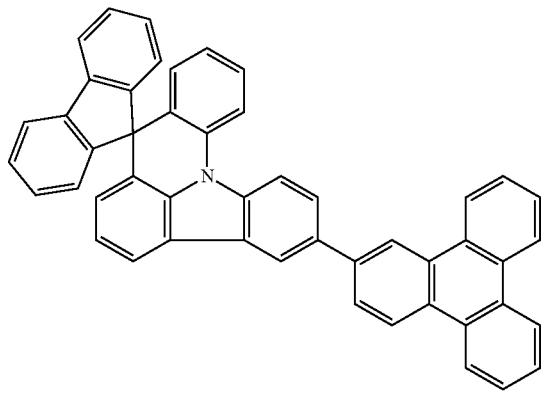
Formula 2-5
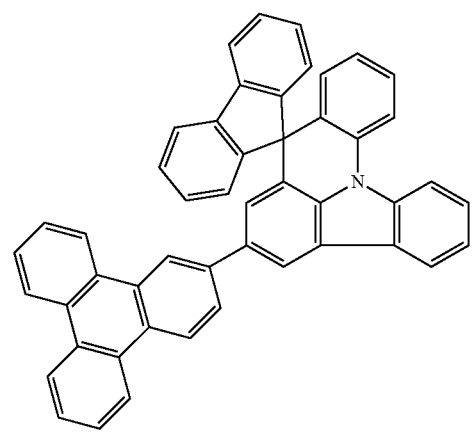
Formula 2-6
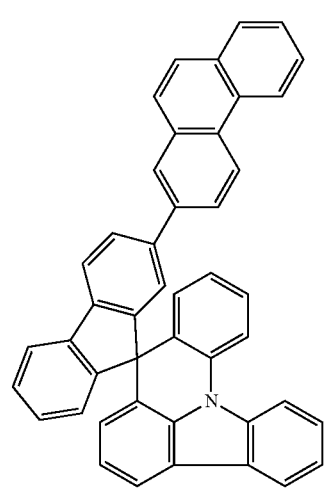
-continued
Formula 2-7
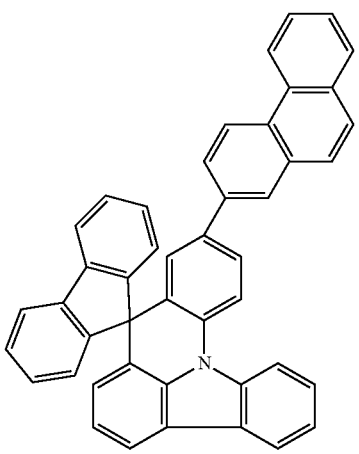
Formula 2-8
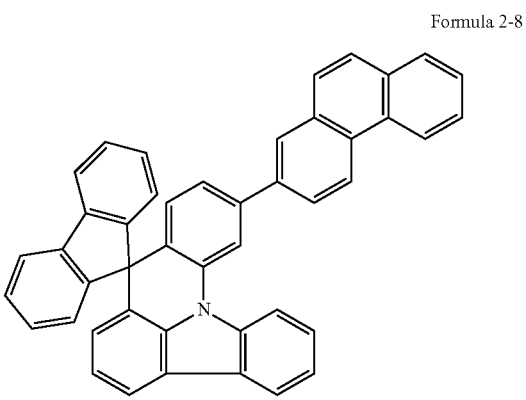
Formula 2-9
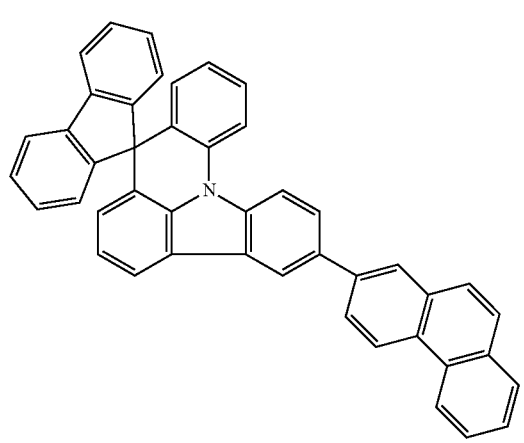

Formula 2-10
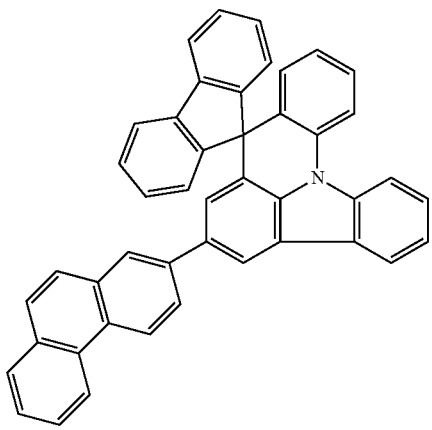
Formula 2-11
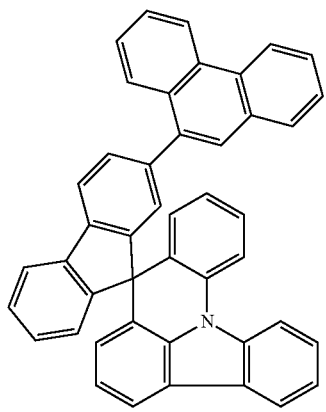
Formula 2-12
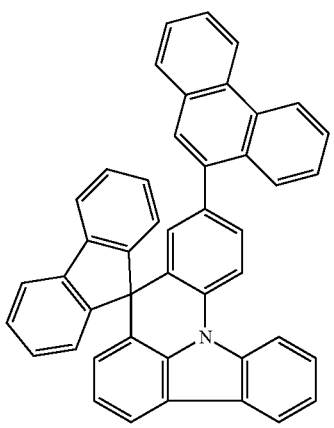
Formula 2-13
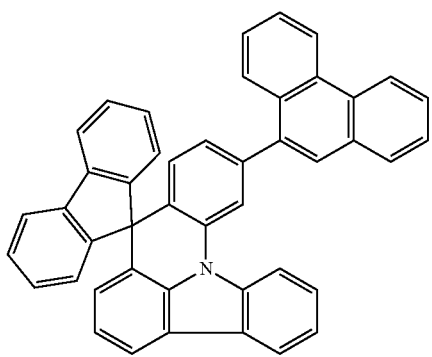
Formula 2-14
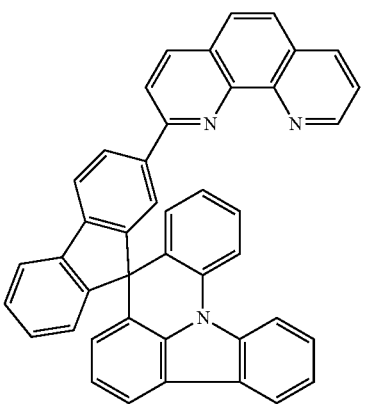
Formula 2-15
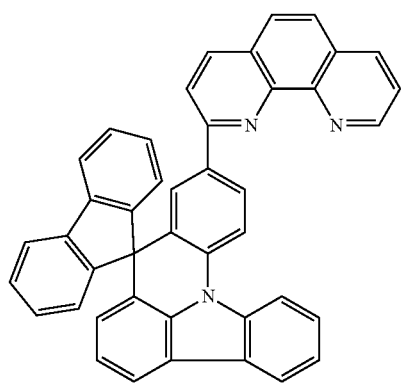
Formula 2-16
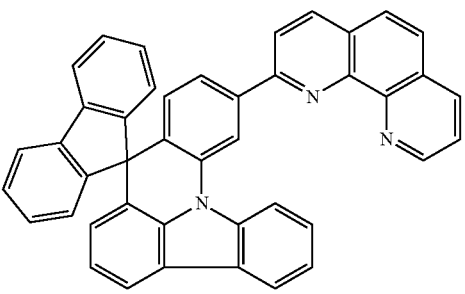
Formula 2-17
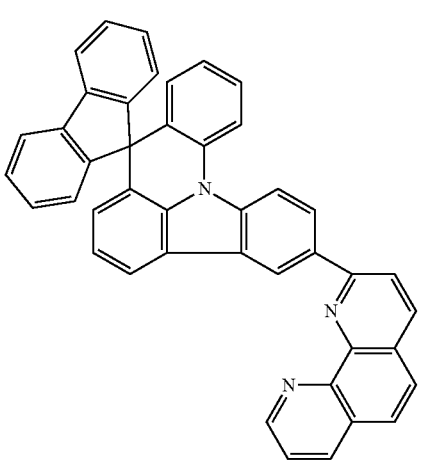

Formula 2-18
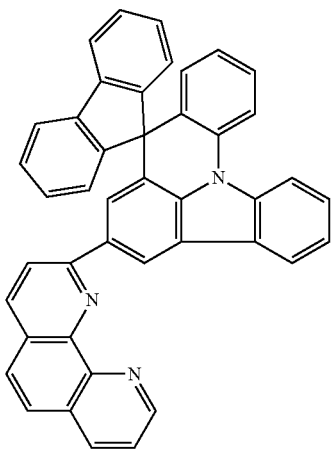
Formula 2-19
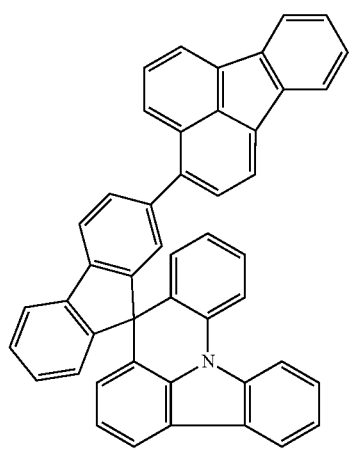
Formula 2-20
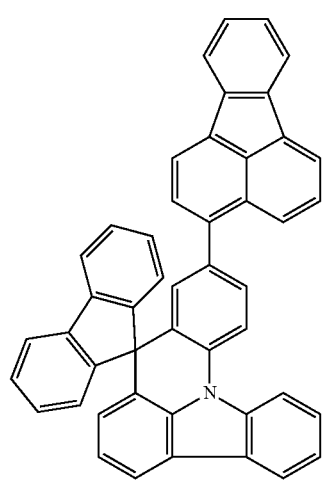
Formula 2-21
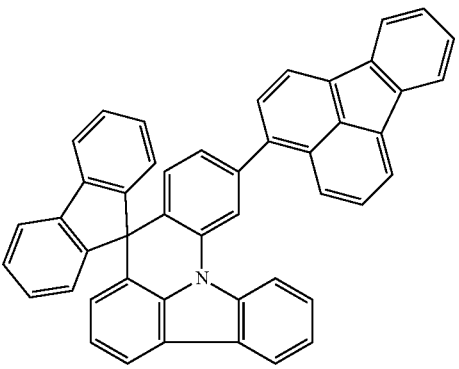
Formula 2-22
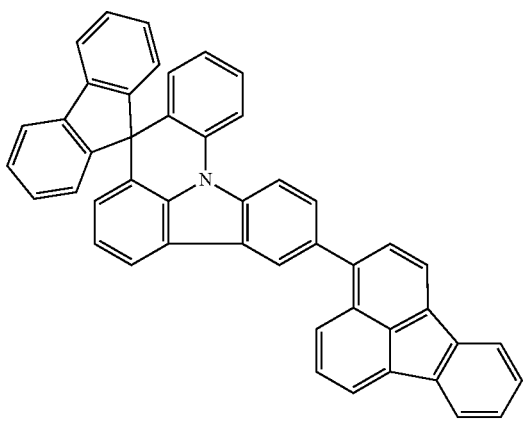
Formula 2-23
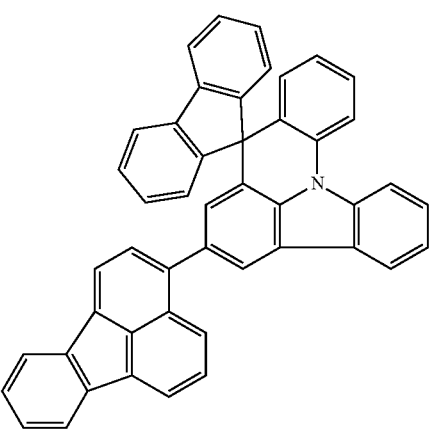

Formula 2-24
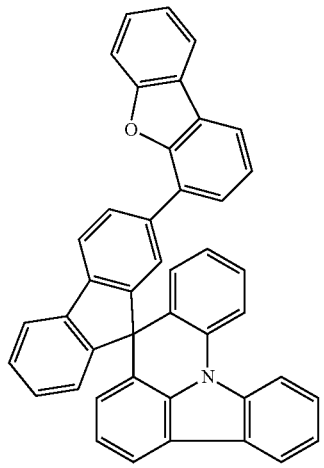
Formula 2-25
Formula 2-26
Formula 2-27
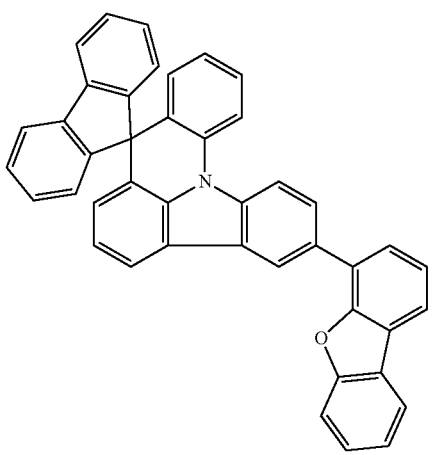
Formula 2-28
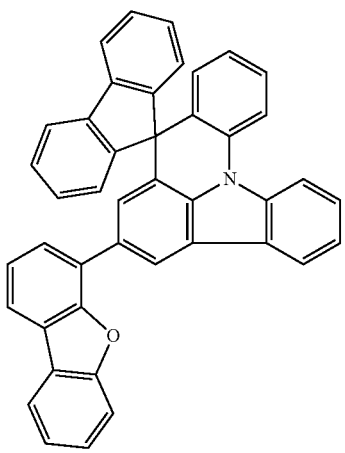
Formula 2-29
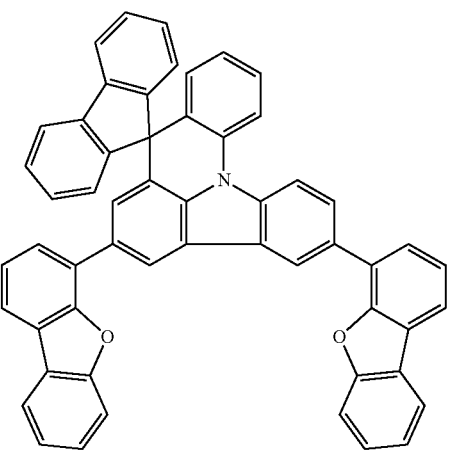
Formula 2-30
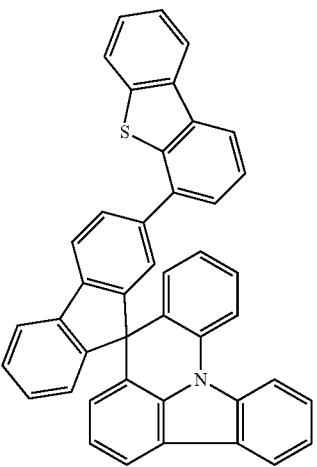

Formula 2-31
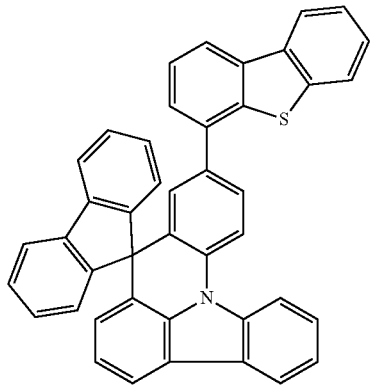
Formula 2-32
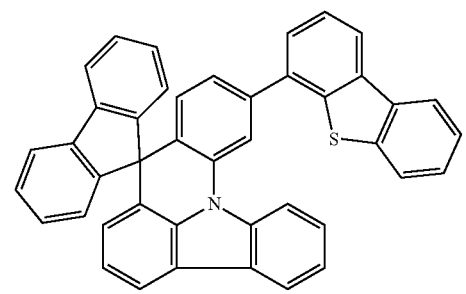
Formula 2-33
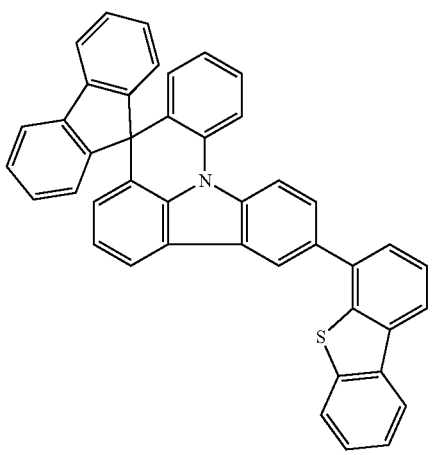
Formula 2-34
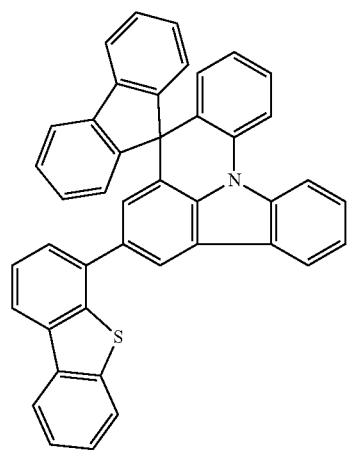
Formula 2-35
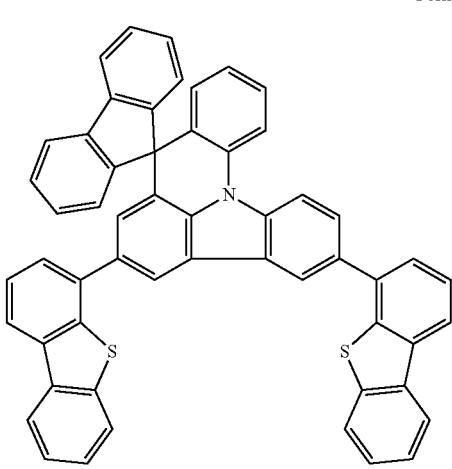
Formula 2-36
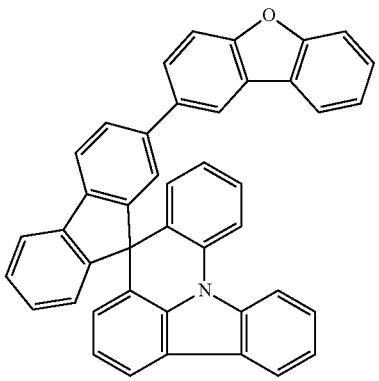
Formula 2-37
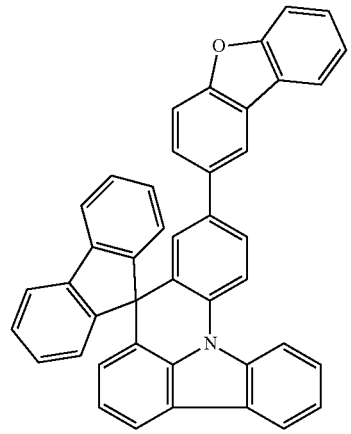
Formula 2-38
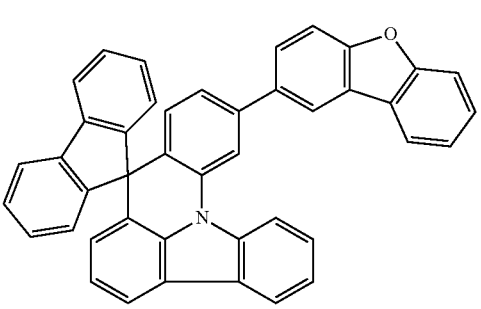

Formula 2-39
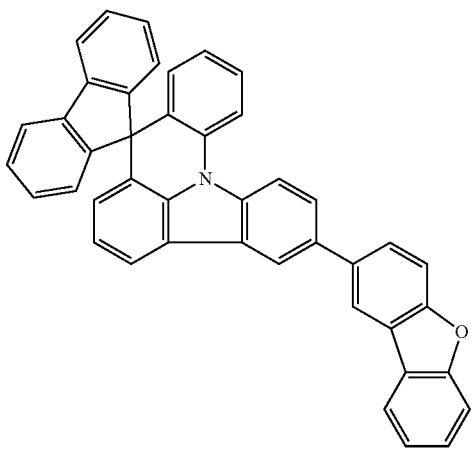
Formula 2-40
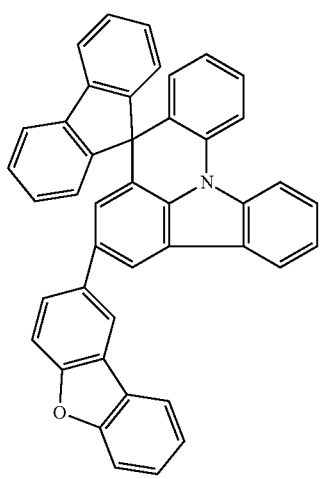
Formula 2-41
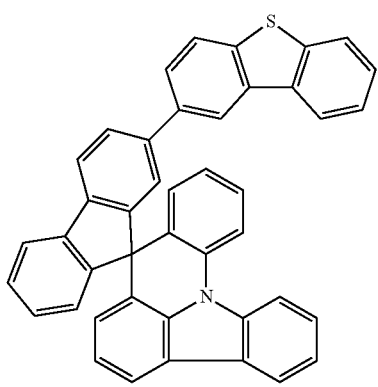
Formula 2-42
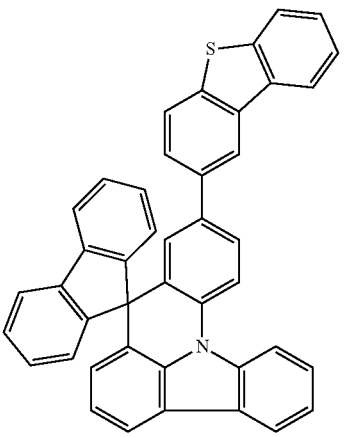
Formula 2-43
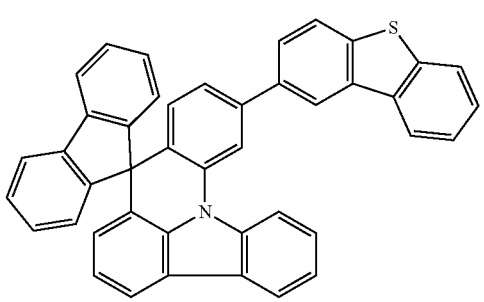
Formula 2-44
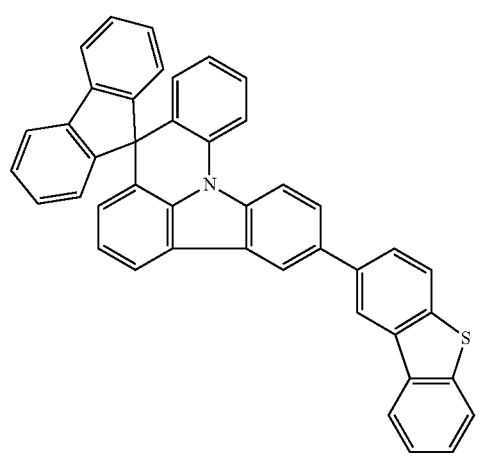

Formula 2-45
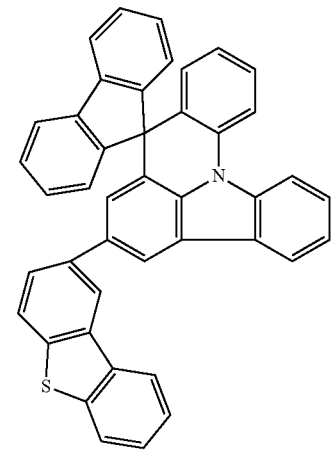
Formula 2-46
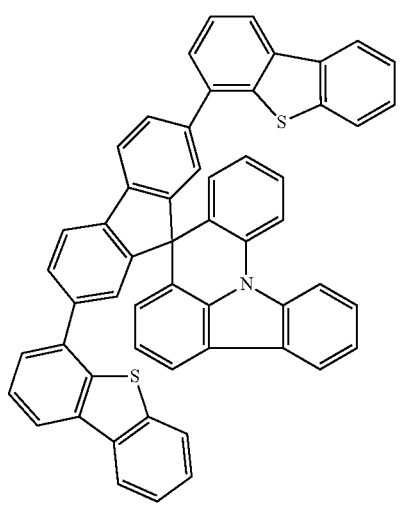
Formula 2-47
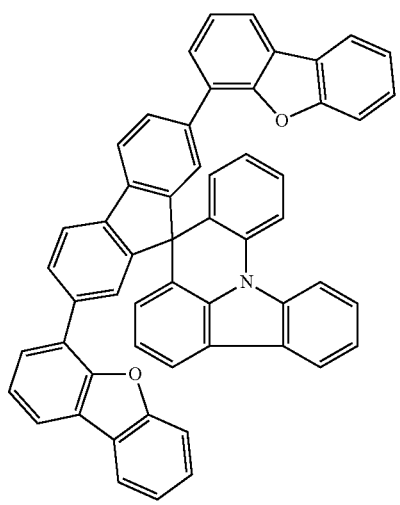
Formula 2-48
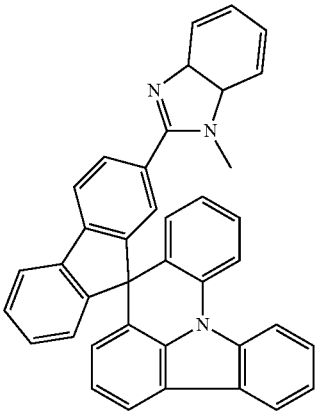
Formula 2-49
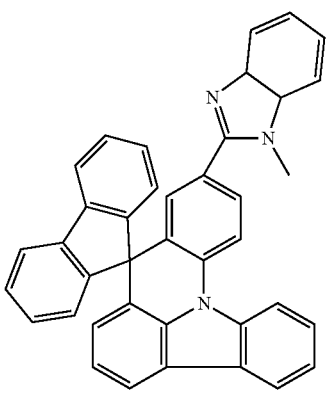
Formula 2-50
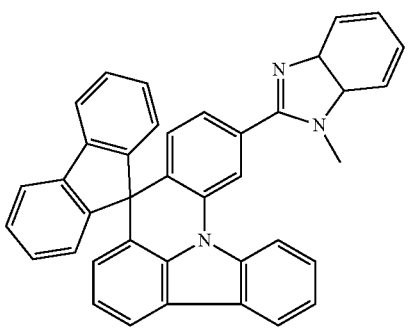
Formula 2-51
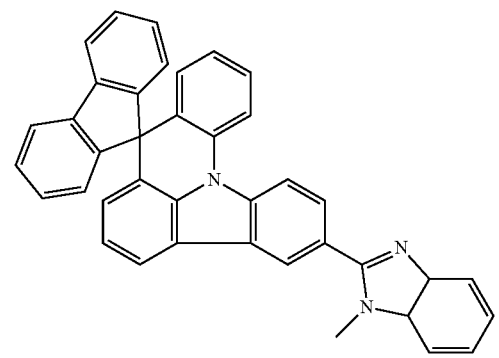

Formula 2-52
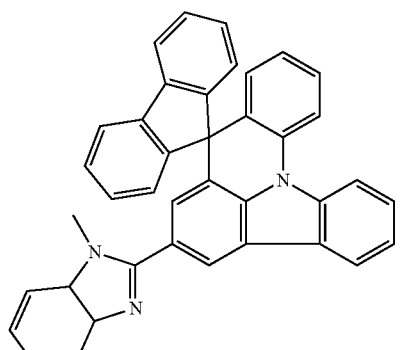
Formula 2-53
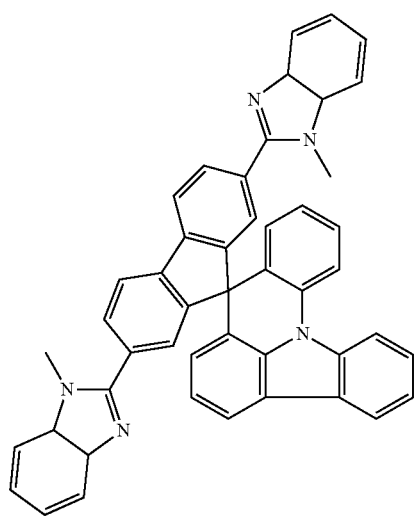
Formula 2-54
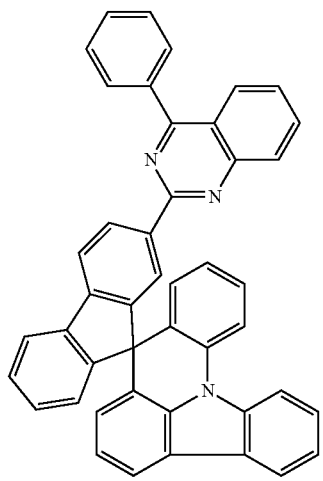
Formula 2-55
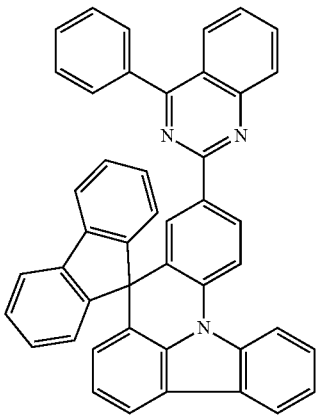
Formula 2-56
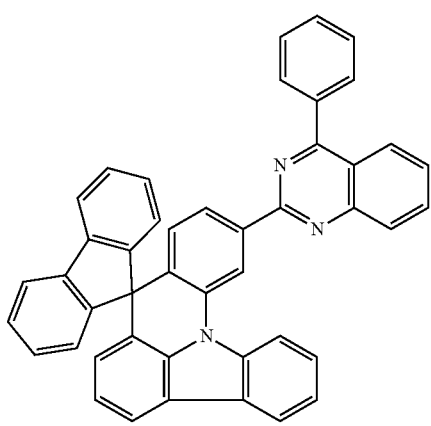
Formula 2-57
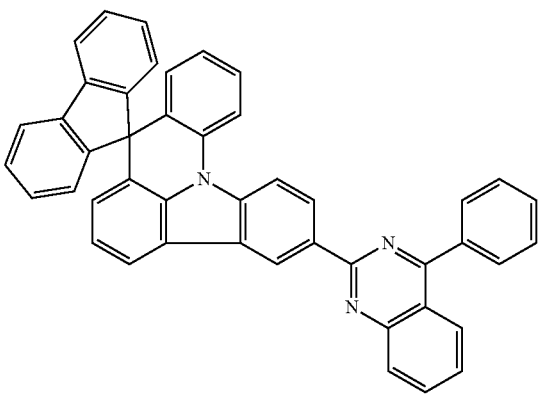

Formula 2-58
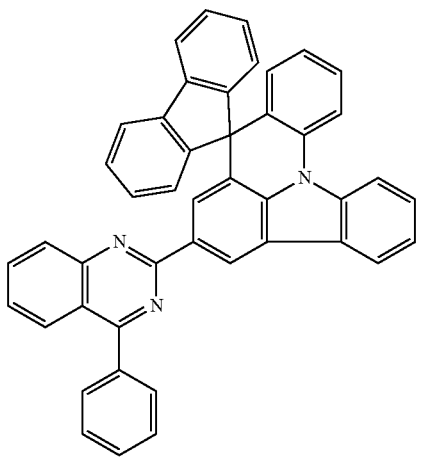
Formula 2-59
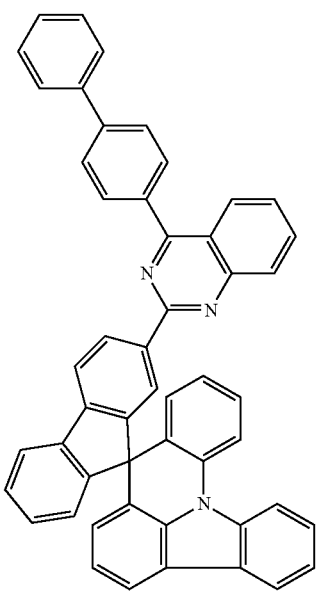
Formula 2-60
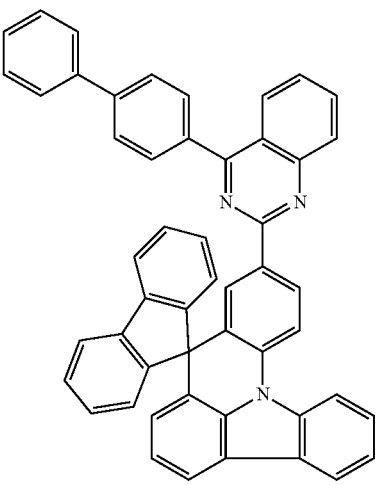
Formula 2-61
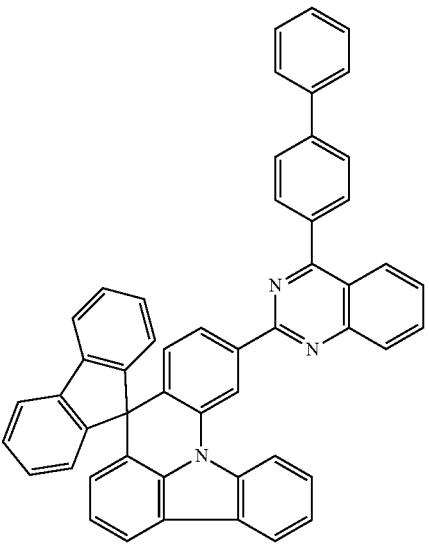
Formula 2-62
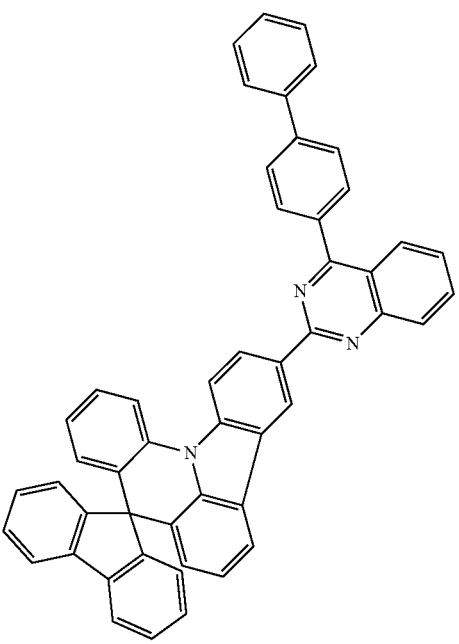

Formula 2-63
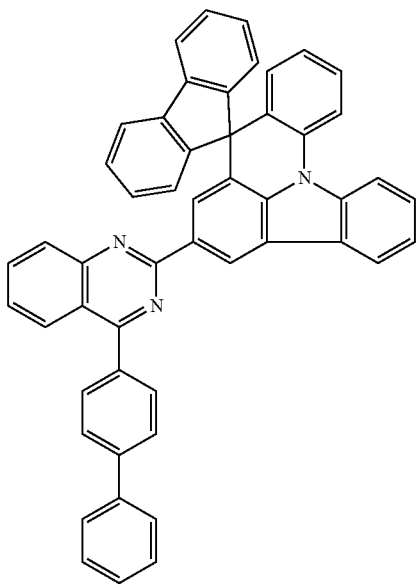
Formula 2-64
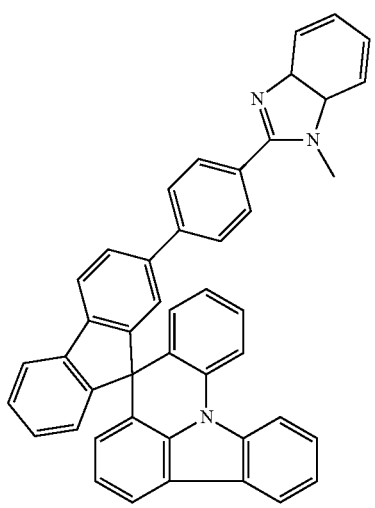
Formula 2-65
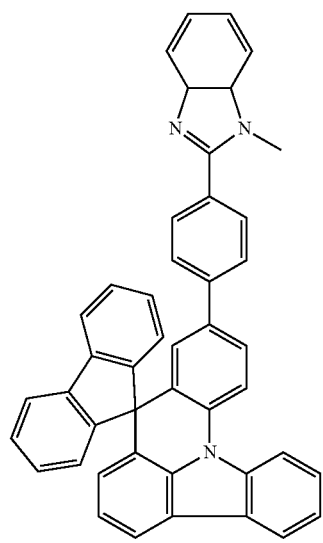
Formula 2-66
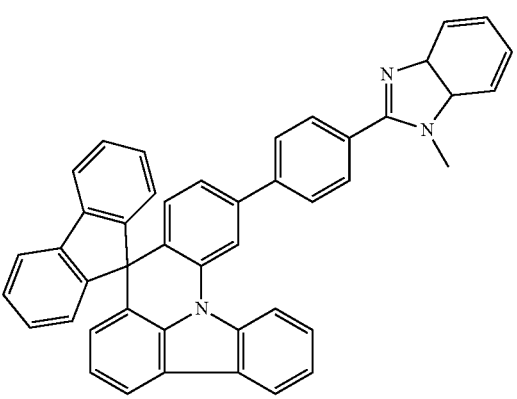
Formula 2-67
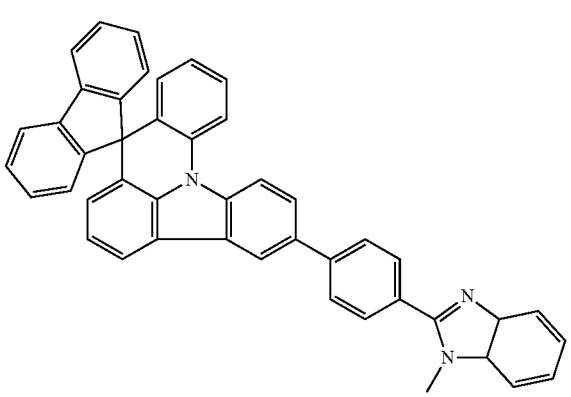
Formula 2-68
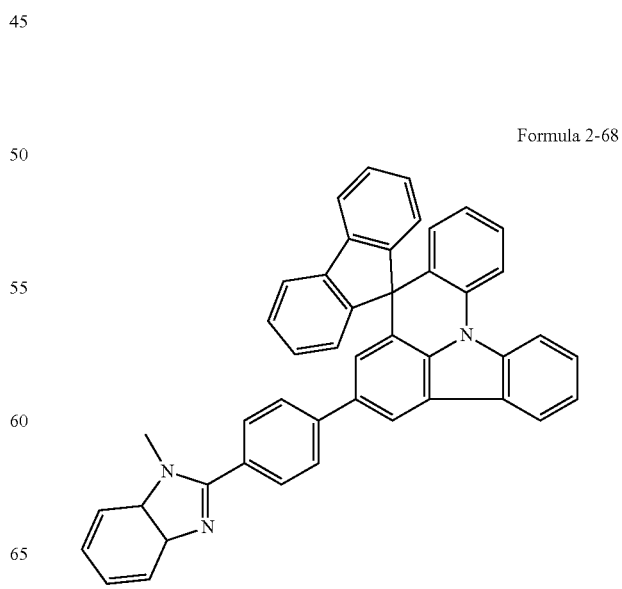

Formula 2-69
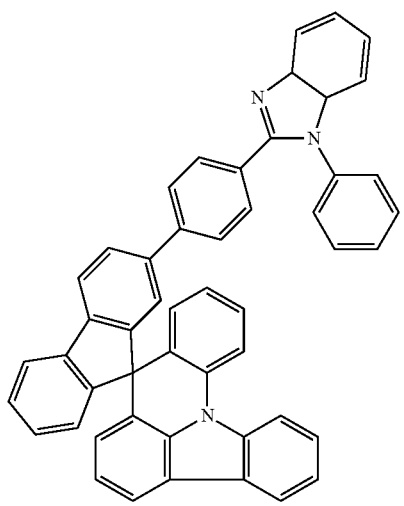
Formula 2-72
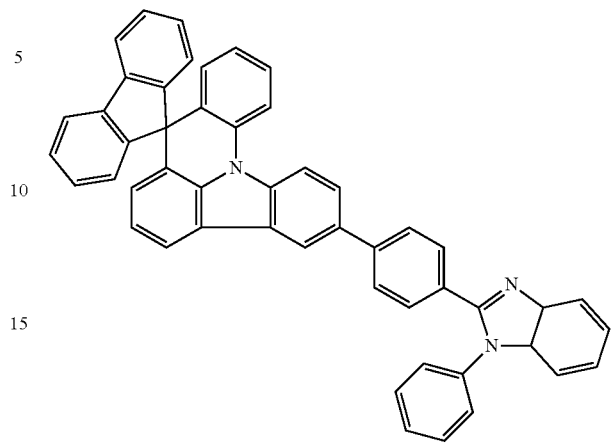
Formula 2-70
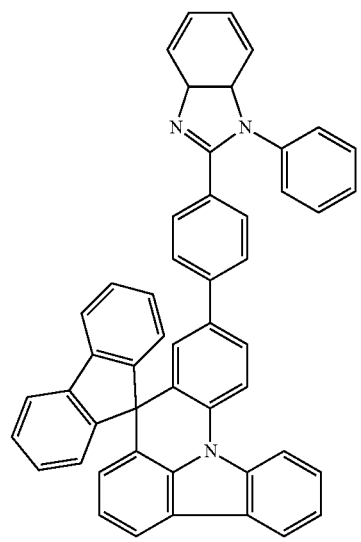
Formula 2-73
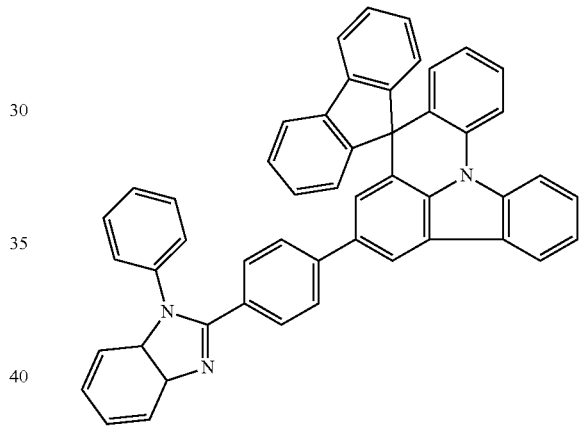
Formula 2-71
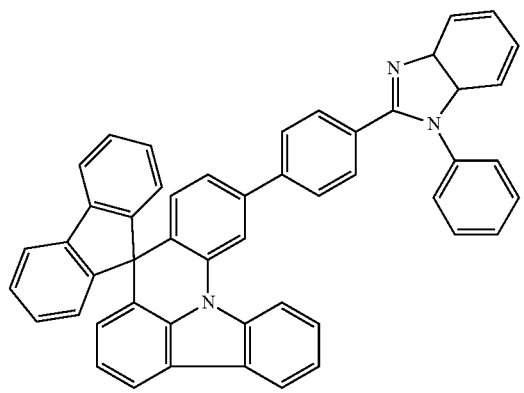
Formula 2-74
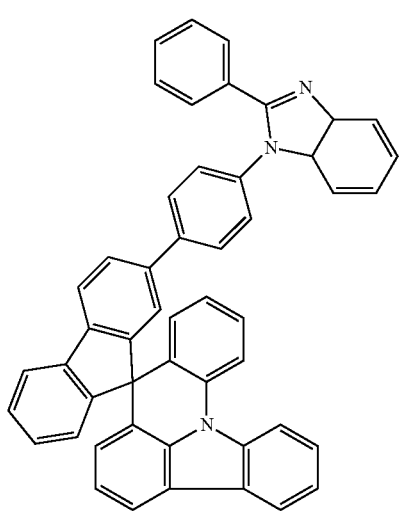

Formula 2-75

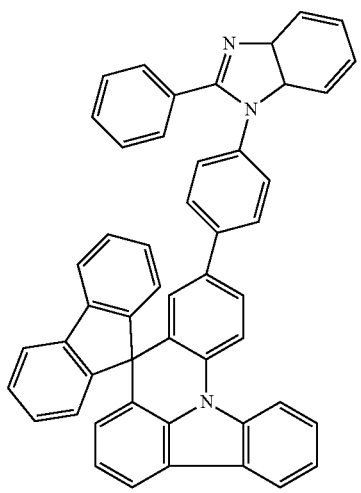

Formula 2-76

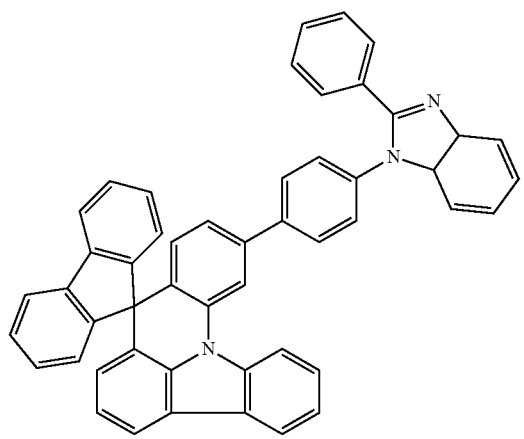

Formula 2-77

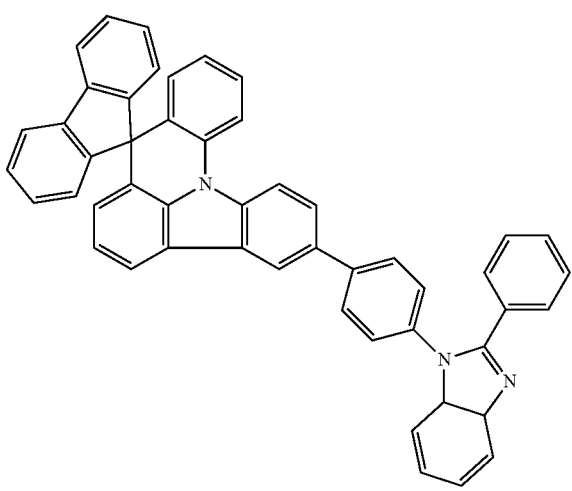

Formula 2-78

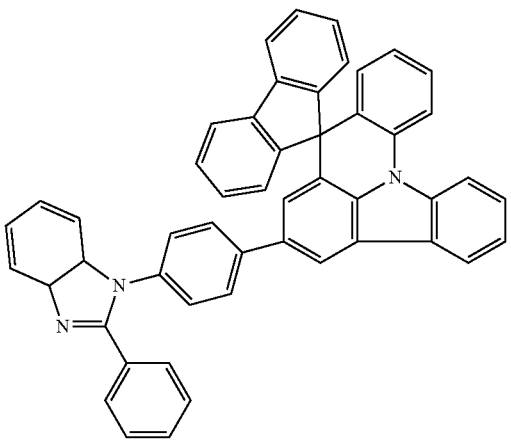

Starting materials, reaction materials, reaction conditions and the like can be modified on the basis of the Preparation Examples described below and the technologies known in the art.

An embodiment of the present disclosure also provides an organic electronic device comprising a first electrode, a second electrode opposite the first electrode, and one or more organic material layers interposed between the first electrode and the second electrode, wherein one or more of the organic material layers comprise the nitrogen-containing heterocyclic compound represented by formula 1.

According to an embodiment of the present disclosure, the organic electronic device may be selected from an organic solar cell, an organic light-emitting device, an organic transistor and an organic photo-conductor.

According to an embodiment of the present disclosure, the organic electronic device may be fabricated by depositing a conductive metal or an alloy thereof on a substrate using a PVD (physical vapor deposition) method such as sputtering or e-beam evaporation to form an anode, forming thereon organic material layers, including a hole-injecting layer, a hole-transporting layer, a light-emitting layer and an electron-transporting layer, and depositing thereon a material capable of acting as a cathode.

In addition, the organic electronic device may also be fabricated by sequentially depositing a cathode material, organic material layers and an anode material on a substrate (International Patent Publication No. WO 2003/012890). However, the fabrication method is not limited to the above methods.

According to an embodiment of the present disclosure, a smaller number of organic material layers can be formed from various polymer materials using a solvent process, for example, spin coating, dip coating, doctor blade coating, screen printing, inkjet printing or heat transfer, in place of the deposition method.

According to an embodiment of the present disclosure, the organic material layers may have a multilayer structure including a hole-injecting layer, a hole-transporting layer, a hole-blocking layer, a light-emitting layer, an electron-blocking layer and an electron-transporting layer, but is not limited thereto, and may alternatively be a monolayer structure.

According to an embodiment of the present disclosure, the organic electronic device may be an organic light-emitting device.

According to an embodiment of the present disclosure, the organic electronic device may be an organic light-emitting device comprising a first electrode, a second electrode opposite the first electrode, and one or more organic material layers, which are interposed between the first electrode and the second electrode and include a light-emitting layer, wherein at least one of the organic material layers comprises the nitrogen-containing heterocyclic compound.

According to an embodiment of the present disclosure, the organic material layers further include one or more selected from the group consisting of a light-emitting layer, a hole-transporting layer, a hole-blocking layer, an electron-blocking layer, an electron transporting layer and an electron-injecting layer.

According to an embodiment of the present disclosure, the organic material layers include a light-emitting layer.

According to an embodiment of the present disclosure, the light-emitting layer comprises the compound represented by formula 1.

According to an embodiment of the present disclosure, the light-emitting layer comprises a host and a dopant.

According to an embodiment of the present disclosure, the host comprises the compound represented by formula 1.

According to an embodiment of the present disclosure, the dopant comprises the compound represented by formula 1.

According to an embodiment of the present disclosure, the organic material layers include a layer that performs both electron transport and light emission.

According to an embodiment of the present disclosure, the organic material layers include a layer that performs all light emission and electron transport and/or electron injection.

When the organic light-emitting device comprises a plurality of organic material layers, the organic material materials may be formed of the same material or different materials.

According to an embodiment of the present disclosure, the organic electronic device may be an organic solar cell.

According to an embodiment of the present disclosure, the organic electronic device may be an organic solar cell comprising a first electrode, a second electrode opposite the first electrode, and one or more organic material layers, which are interposed between the first electrode and the second electrode and include a photoactive layer, wherein at least one of the organic material layers comprises the nitrogen-containing heterocyclic compound.

According to an embodiment of the present disclosure, the organic layers include a photoactive layer.

According to an embodiment of the present disclosure, the organic material layers include one or more selected from the group consisting of a photoactive layer, an electron donor and an electron acceptor.

According to an embodiment of the present disclosure, the organic material layers are photoactive layers having an electron donor and/or an electron acceptor.

According to an embodiment of the present disclosure, when the organic solar cell receives a photon from an external light source, an electron and a hole are generated between the electron donor and the electron acceptor. The generated hole is transported to the anode through the electron donor layer.

According to an embodiment of the present disclosure, the organic layers may include two or more materials.

According to an embodiment of the present disclosure, the organic solar cell may further include an additional organic material layer. The organic solar cell may comprise an organic material having various functions in order to reduce the number of organic material layers therein.

According to an embodiment of the present disclosure, the organic electronic device may be an organic transistor.

An embodiment of the present disclosure provides an organic transistor comprising a source, a drain, a gate and one or more organic material layers.

According to an embodiment of the present disclosure, the organic electronic device may be an organic transistor comprising a source, a drain, a gate and one or more organic material layers, wherein one or more of the organic layers may comprise the above nitrogen-containing heterocyclic compound.

According to an embodiment of the present disclosure, the organic transistor may further comprise an insulating layer. The insulating layer may be located over a substrate and the gate.

According to an embodiment of the present disclosure, the organic electronic device may be an organic photo-conductor.

According to an embodiment of the present disclosure, the organic electronic device may be an organic photo-conductor comprising a first electrode, a second electrode opposite the first electrode, and one or more organic material layers, which are interposed between the first electrode and the second electrode and an organic photosensitive layer, wherein at least one of the organic material layers comprises the above nitrogen-containing heterocyclic compound.

According to an embodiment of the present disclosure, the organic material layers further comprise a UV light stabilizer.

According to an embodiment of the present disclosure, the organic photo-conductor may, for example, be provided in the form of a plate, a flexible belt, a disk, a rigid drum, or a sheet around a rigid or compliant drum. The rigid drum is generally used in commercial applications.

According to an embodiment of the present disclosure, the organic photo-conductor may comprise, for example, an electrically conductive substrate and a photoconductive element in the form of one or more layers. The organic photo-conductor can comprise both a charge transport material and a charge-generating compound in a polymeric binder, which may or may not be in the same layer.

Similarly, an electron transport compound and the charge-generating compound may or may not be in the same layer. If the electron transport compound and the charge-generating compound are present in different layer, the electron transport compound may be in an overcoat layer opposite the electrically conductive substrate. Alternatively, the electron transport compound may be in the undercoat layer, like the electrically conductive substrate.

The substrate may be a glass substrate or a transparent plastic substrate, which has superior transparency, surface flatness, ease of handling and waterproofness, but is not limited thereto, and may be any substrate that is generally used in organic electronic devices.

The first electrode may be an anode, and the second electrode may be a cathode.

The first electrode may be a cathode, and the second electrode may be an anode.

The anode material is preferably a material having a high work function, so that holes can be easily injected into the organic layers. Specific examples of an anode material that may be used in the present disclosure include, but are not limited to, metals such as vanadium, chromium, copper, zinc or gold, or alloys thereof; metal oxides such as zinc oxide, indium oxide, indium tin oxide (ITO) or indium zinc oxide (IZO); metal/oxide combinations such as ZnO: Al or $SNO_2$: Sb; and conductive polymers such as poly(3-methylthiophene), poly[3,4-(ethylene-1,2-dioxy)thiophene](PEDOT), polypyrrole and polyaniline.

The cathode material is preferably a material having a low work function, so that electrons are easily injected into the organic layers. Specific examples of the cathode material include, but are not limited to, metals such as magnesium, calcium, sodium, potassium, titanium, indium, yttrium, lithium, gadolinium, aluminum, silver, tin and lead, or alloys thereof; and multilayer materials such as LiF/Al or LiO$_2$/Al.

The source, the drain and the gate may be made of the materials exemplified as the anode or cathode materials.

The material of the hole-injecting material is a material that can easily receive holes from the anode at a low voltage, and the HOMO (highest occupied molecular orbital) of the hole-injecting material is preferably between the work function of the anode material and the HOMO of the surrounding organic material layers. Specific examples of the hole-injecting layer material include, but are not limited to, metal porphyrin, oligothiophene, and arylamine-based organic materials, hexanitrile hexaazatriphenylene and quinacridone-based organic materials, perylene-based organic materials, anthraquinone, polyaniline-based or polythiophene-based conductive polymers and the like.

The material of the hole-transporting layer is preferably a material having high hole mobility, which is capable of transferring holes from the anode or the hole-injecting layer to the light-emitting layer. Specific examples of the hole-transporting layer material include, but are not limited to, arylamine-based organic materials, conductive polymers, and block copolymers having both conjugated portions and non-conjugated portions.

The material of the light-emitting layer is a material capable of emitting visible light by receiving holes and electrons from the hole-transporting layer and the electron-transporting layer, respectively, and combining the received holes and electrons, and is preferably a material having high quantum efficiency for fluorescence and phosphorescence. Specific examples of the light-emitting layer material include, but are not limited to, an 8-hydroxyquinoline aluminum complex (Alq$_3$); carbazole-based compounds; dimerized styryl compounds; BAlq; 10-hydroxybenzoquinoline-metal compounds; benzoxazole-, benzthiazole- and benzimidazole-based compounds; poly(p-phenylenevinylene) (PPV)-based polymers; spiro compounds; and compounds such as polyfluorene and rubrene.

The material of the electron-transporting layer is a material that can easily receive electrons from the cathode and transfer the received electrons to the light-emitting layer. It is preferably a material having high electron mobility. Specific examples of the electron-transporting material include, but are not limited to, a 8-hydroxyquinoline aluminum complex; complexes including Alq; organic radical compounds; and hydroxyflavone-metal complexes.

The organic electronic device according to the present disclosure may be a front side light-emitting type, a rear side light-emitting type or a double-side light-emitting type, depending on the material used.

Node for Disclosure

Hereinafter, the present disclosure will be described in further detail with reference to Preparation Examples and Experimental Examples. It is to be understood, however, that these Preparation Examples and Experimental Examples are for illustrative purposes only, and are not intended to limit the scope of the present disclosure.

Preparation Example 1

Preparation of Compound of Formula 2-29

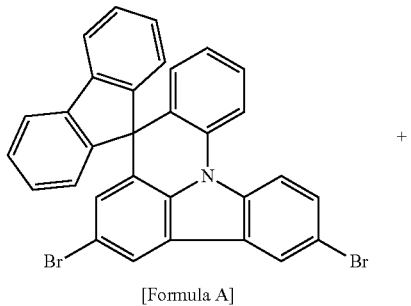

[Formula A]

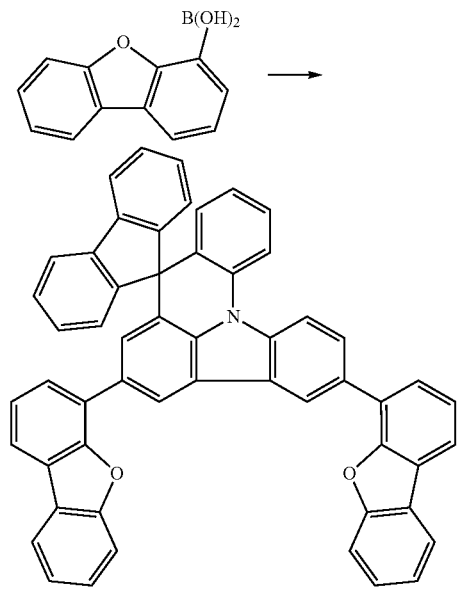

[Formula 2-29]

Compound A (7.6 g, 13.5 mmol) and 4-dibenzofuran boronic acid (6.3 g, 29.7 mmol) were completely dissolved in tetrahydrofuran (THF) (100 mL), and then a 2M aqueous solution of potassium carbonate (180 mL) was added thereto, and Pd(PPh$_3$)$_4$ (0.5 g, 3 mol %) was added thereto. Then, the mixture was stirred under reflux for 24 hours. The temperature of the mixture was lowered to room temperature, the aqueous layer was removed, and the organic layer was filtered. The resulting solid was purified by silica gel column chromatography, thereby obtaining the compound of formula 2-29 (3.3 g, 33%).

MS: [M+H]$^+$=738

Figure 3:
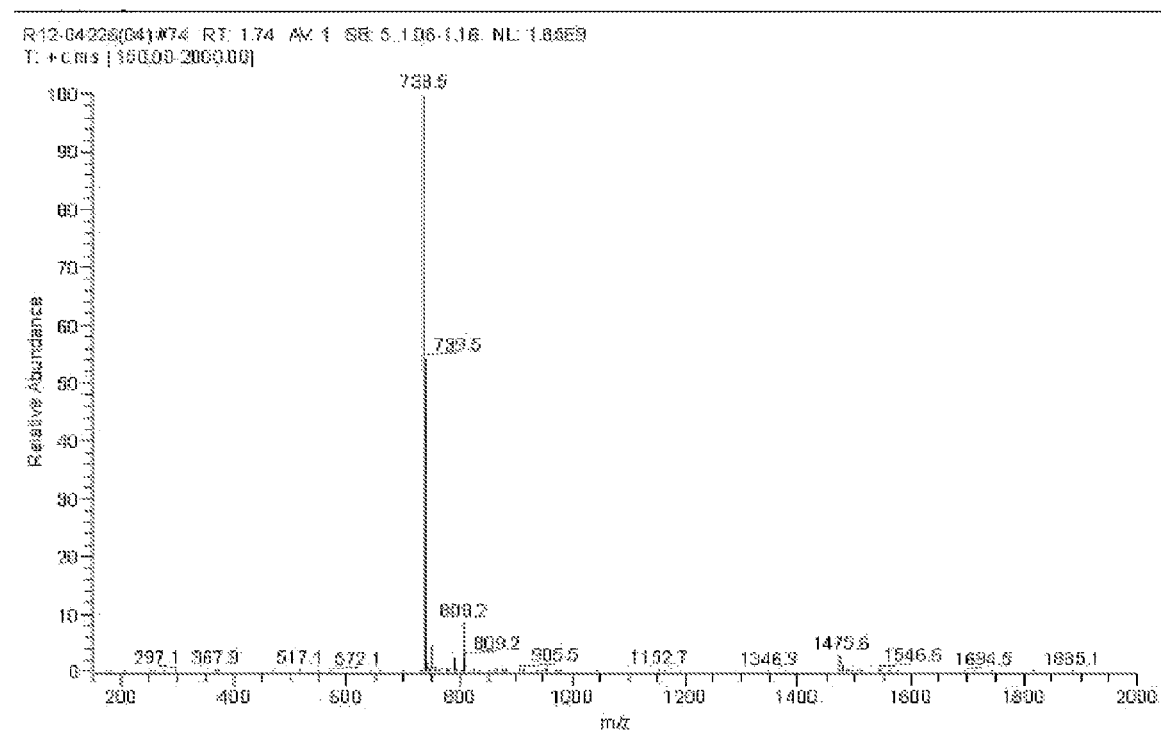
FIG. 3 shows the mass spectrum of the compound of formula 2-29, synthesized in Preparation Example 1.

FIG. 3 shows the mass spectrum of the compound of formula 2-29, synthesized in Preparation Example 1.

Preparation Example 2

Preparation of Compound of Formula 2-35

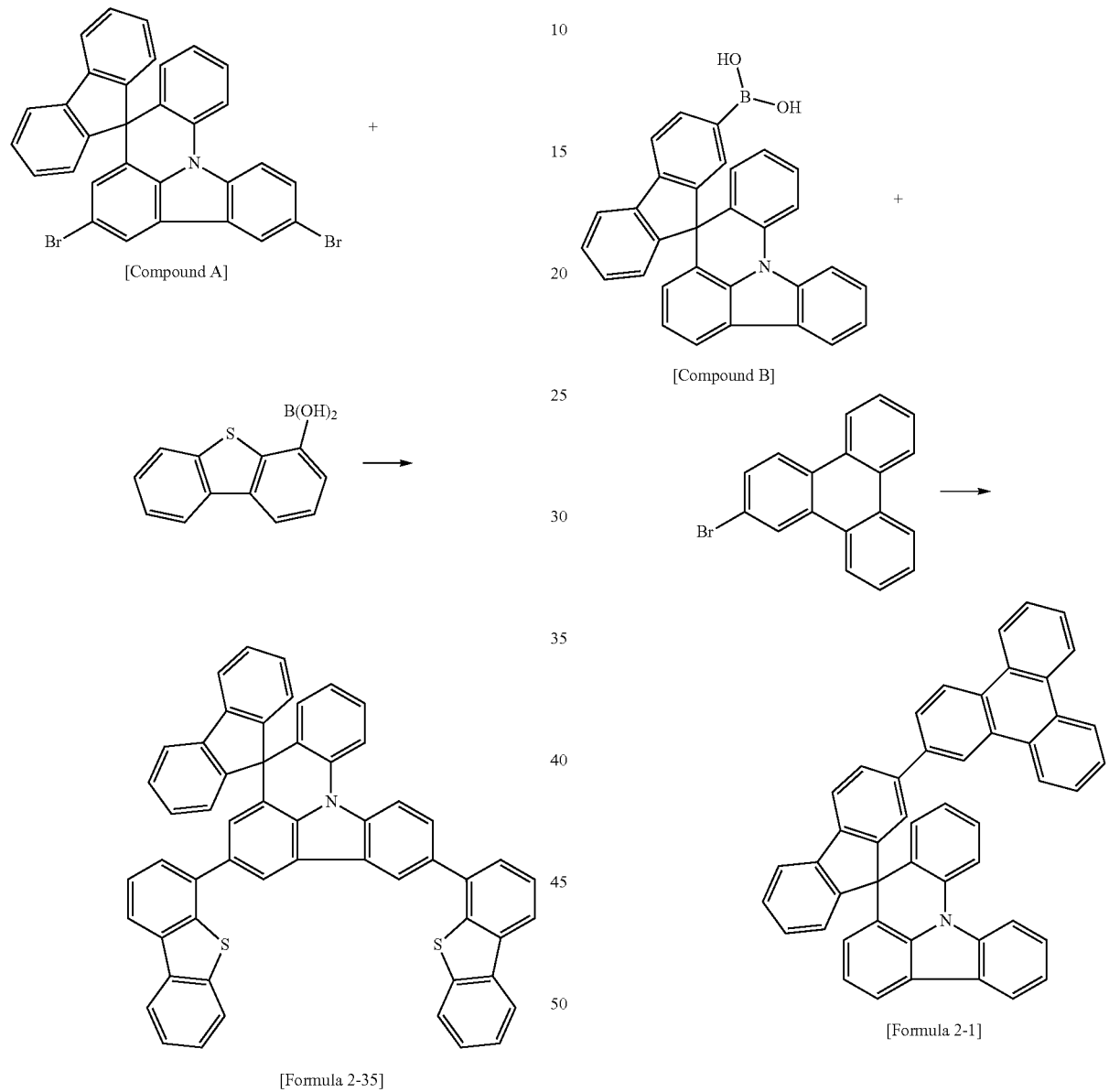

[Formula 2-1]

Figure 4:
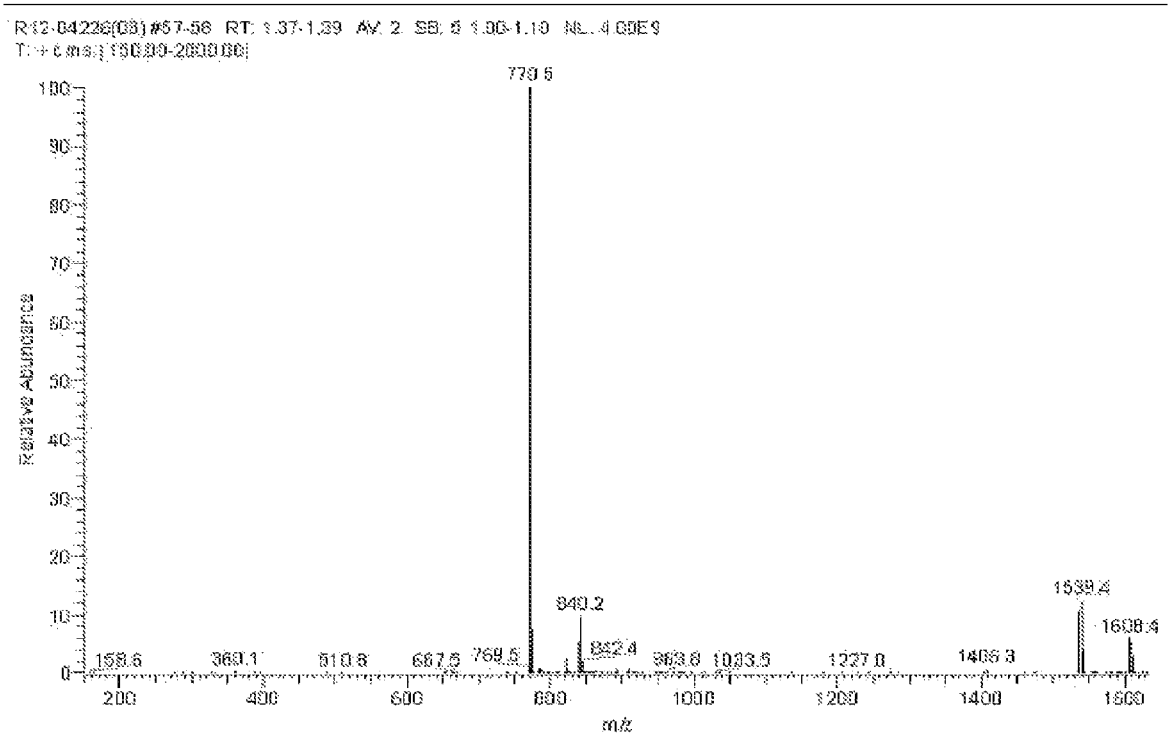
FIG. 4 shows the mass spectra of the compound of formula 2-35, synthesized in Preparation Example 2.

FIG. 4 shows the mass spectrum of the compound of formula 2-35, synthesized in Preparation Example 2.

Preparation Example 3

Preparation of Compound of Formula 2-1

Compound A (8.0 g, 14.2 mmol) and 4-dibenzothiophene boronic acid (7.1 g, 31.2 mmol) were completely dissolved in tetrahydrofuran (THF) (100 mL), and then a 2M aqueous solution of potassium carbonate (180 mL) was added thereto, and Pd(PPh$_3$)$_4$ (0.5 g, 3 mol %) was added thereto. Then, the mixture was stirred under reflux for 24 hours. The temperature of the mixture was lowered to room temperature, the aqueous layer was removed, and the organic layer was filtered. The resulting solid was purified by silica gel column chromatography, thereby obtaining the compound of formula 2-35 (4.9 g, 45%).

MS: [M+H]$^+$=771

Compound B (10 g, 23.3 mmol) and 2-bromotriphenylene (6.2 g, 20.2 mmol) were completely dissolved in tetrahydrofuran (THF) (300 mL), and then a 2M aqueous solution of potassium carbonate (180 mL) was added thereto, and Pd(PPh$_3$)$_4$ (0.7 g, 3 mol %) was added thereto. Then, the mixture was stirred under reflux for 24 hours. The temperature of the mixture was lowered to room temperature, the aqueous layer was removed, and the organic layer was filtered. The resulting solid was purified by silica gel column chromatography, thereby obtaining the compound of formula 2-1 (7.4 g, 50%).

MS: [M+H]$^+$=632

Figure 5:
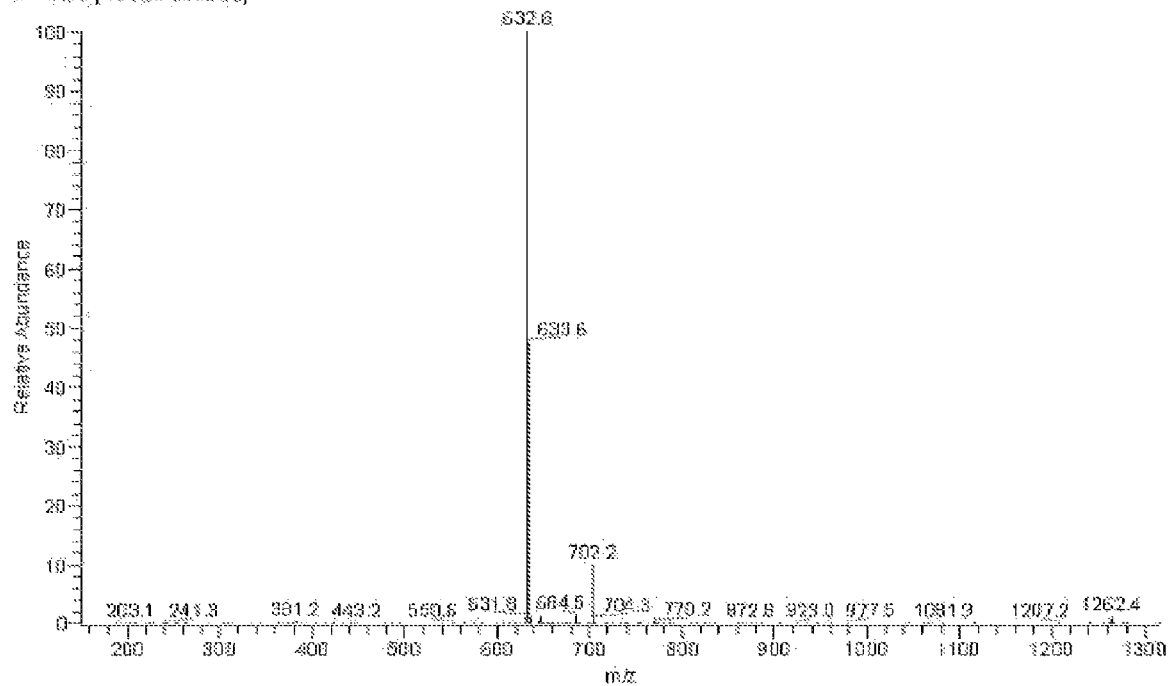
FIG. 5 shows the mass spectra of the compound of formula 2-1, synthesized in Preparation Example 3.

FIG. 5 shows the mass spectrum of the compound of formula 2-1, synthesized in Preparation Example 3.

Preparation Example 4

Preparation of Compound of Formula 2-3

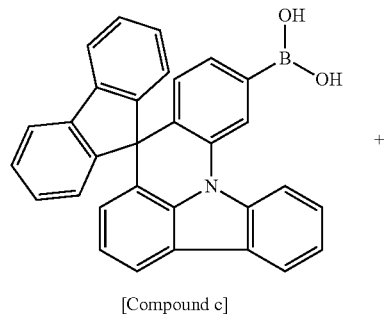
[Compound c]

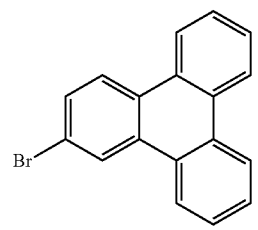

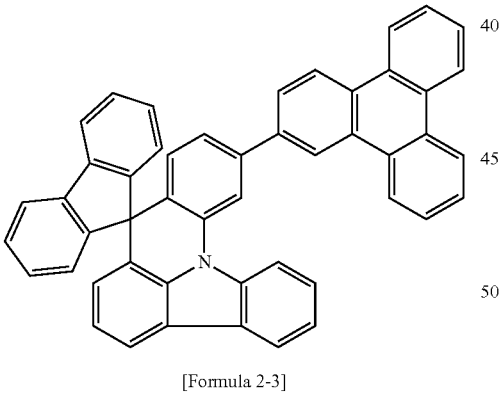
[Formula 2-3]

Compound c (8.4 g, 18.8 mmol) and 2-bromotriphenylene (5.8 g, 18.8 mmol) were completely dissolved in tetrahydrofuran (THF) (300 mL), and then a 2M aqueous solution of potassium carbonate (180 mL) was added thereto, and Pd(PPh$_3$)$_4$ (0.35 g, 3 mol %) was added thereto. Then, the mixture was stirred under reflux for 24 hours. The temperature of the mixture was lowered to room temperature, the aqueous layer was removed, and the organic layer was filtered. The resulting solid was purified by silica gel column chromatography, thereby obtaining the compound of formula 2-3 (3.6 g, 30%).
MS: [M+H]$^+$=632

Figure 6:
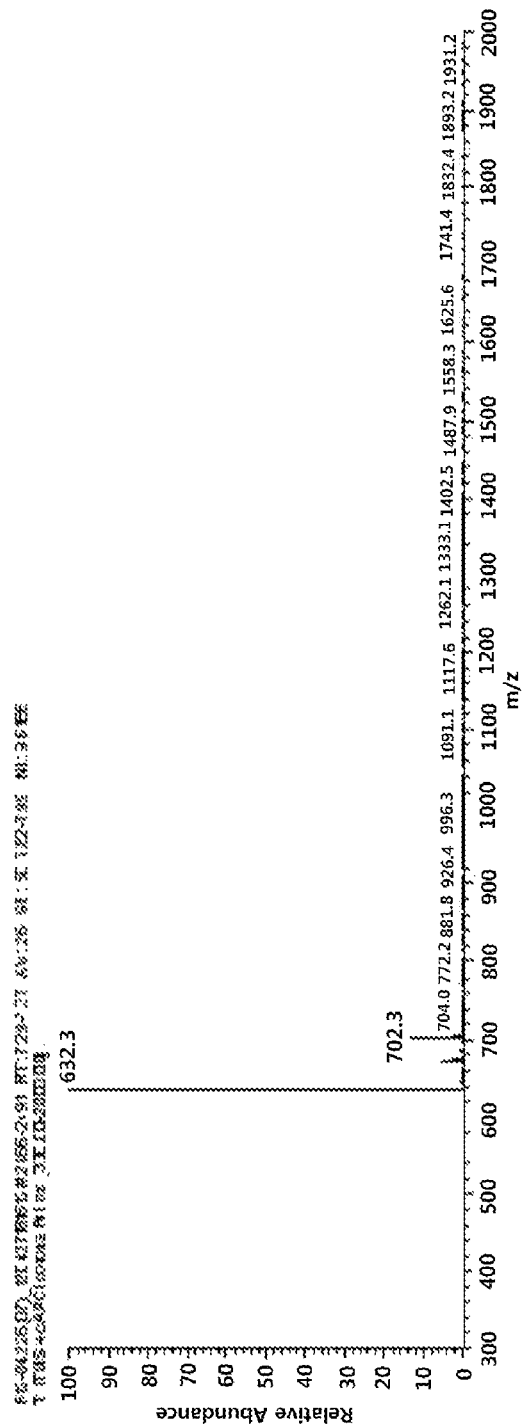
FIG. 6 shows the mass spectra of the compound of formula 2-3, synthesized in Preparation Example 4.

FIG. 6 shows the mass spectrum of the compound of formula 2-3, synthesized in Preparation Example 4.

Preparation Example 5

Preparation of Compound of Formula 2-16

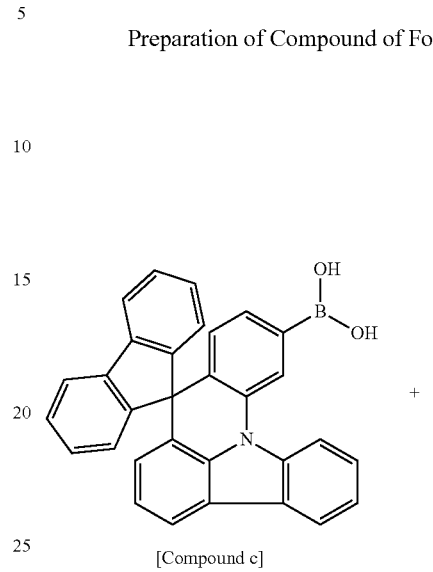
[Compound c]

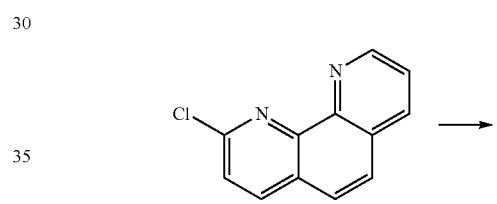

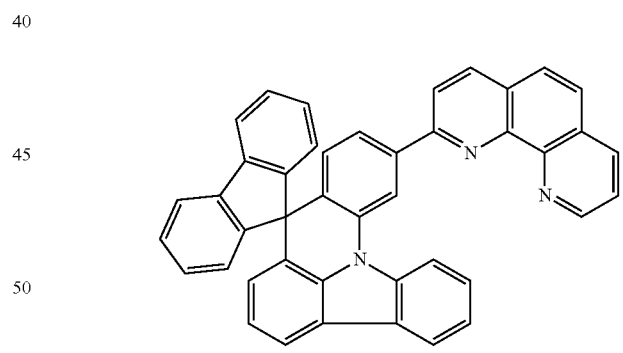
[Compound 2-16]

Compound c (8.4 g, 18.8 mmol) and 2-chloro-1,10-phenanthroline (4.4 g, 20.7 mmol) were completely dissolved in tetrahydrofuran (THF) (100 mL), and then a 2M aqueous solution of potassium carbonate (50 mL) was added thereto, and Pd(PPh$_3$)$_4$ (0.65 g, 3 mol %) was added thereto. Then, the mixture was stirred under reflux for 24 hours. The temperature of the mixture was lowered to room temperature, the aqueous layer was removed, and the organic layer was filtered. The resulting solid was purified by silica gel column chromatography, thereby obtaining the compound of formula 2-16 (4.9 g, 45%).
MS: [M+H]$^+$=584

Figure 7:
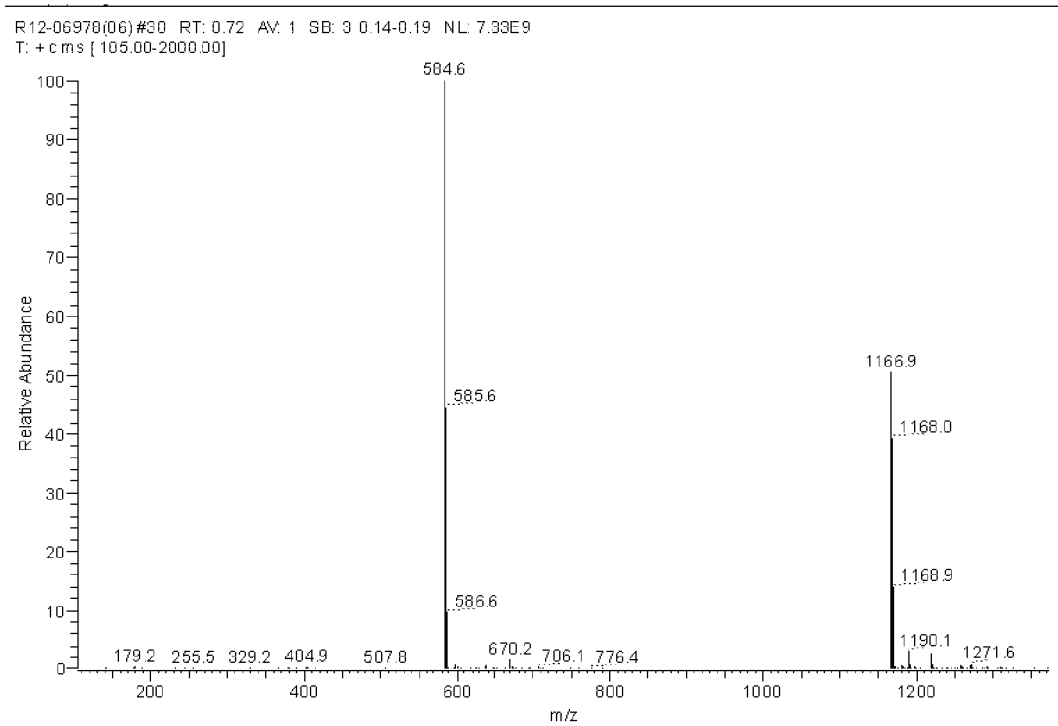
FIG. 7 shows the mass spectra of the compound of formula 2-16, synthesized in Preparation Example 5.

FIG. 7 shows the mass spectrum of the compound of formula 2-16, synthesized in Preparation Example 5.

Figure 8:
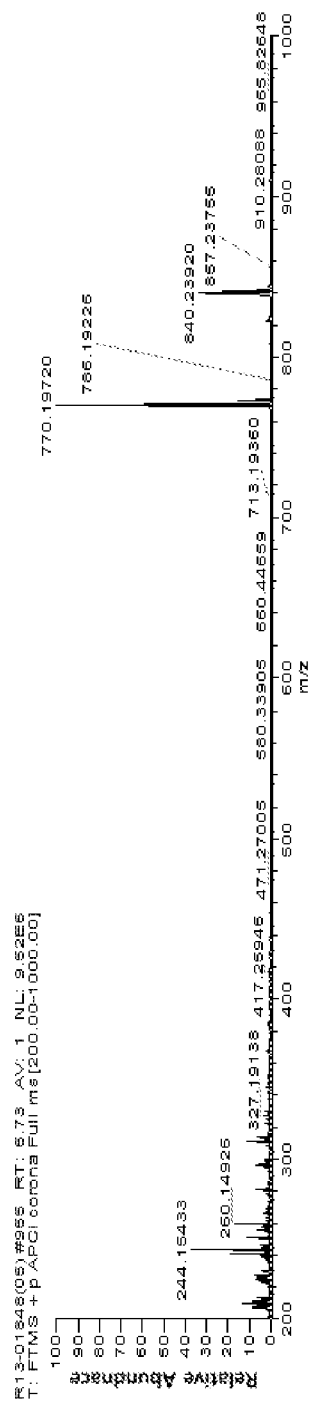
FIG. 8 shows the mass spectra of the compound of formula 2-9, synthesized in Preparation Example 6.

FIG. 8 shows the mass spectrum of the compound of formula 2-46, synthesized in Preparation Example 6.

Preparation Example 6

Preparation of Compound of Formula 2-46

Preparation Example 7

Preparation of Compound of Formula 2-48

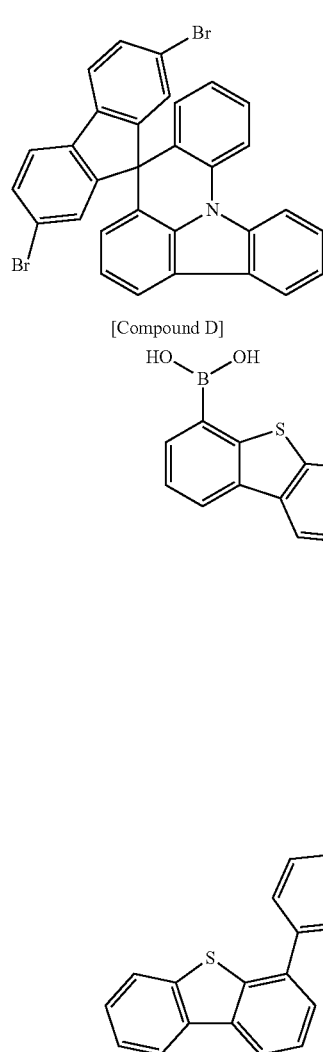

[Compound 2-46]

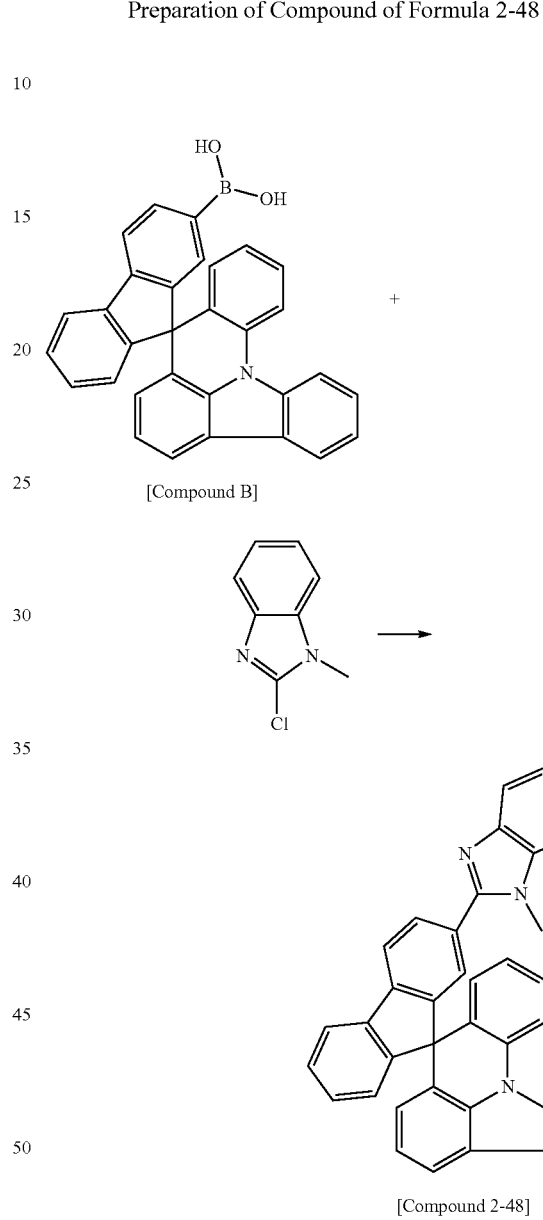

[Compound 2-48]

Compound D (10.0 g, 17.8 mmol) and 4-dibenzothiopheneboronic acid (8.9 g, 39.1 mol) were completely dissolved in tetrahydrofuran (THF) (300 mL), and then a 2M aqueous solution of potassium carbonate (50 mL) was added thereto, and Pd(PPh$_3$)$_4$ (0.4 g, 3 mol %) was added thereto. Then, the mixture was stirred under reflux for 24 hours. The temperature of the mixture was lowered to room temperature, the aqueous layer was removed, and the organic layer was filtered. The resulting solid was purified by silica gel column chromatography, thereby obtaining the compound of formula 2-46 (3.6 g, 25%).

MS: [M+H]$^+$=770

Compound B (9 g, 20.0 mmol) and 2-chloro-1-methyl-1H-benzoimidazole (3.7 g, 22.0 mmol) were completely dissolved in tetrahydrofuran (THF) (100 mL), and then a 2M aqueous solution of potassium carbonate (50 mL) was added thereto, and Pd(PPh$_3$)$_4$ (0.7 g, 3 mol %) was added thereto. Then, the mixture was stirred under reflux for 24 hours. The temperature of the mixture was lowered to room temperature, the aqueous layer was removed, and the organic layer was filtered. The resulting solid was purified by silica gel column chromatography, thereby obtaining the compound of formula 2-48 (5.6 g, 52%).

MS: [M+H]$^+$=536

Figure 9:
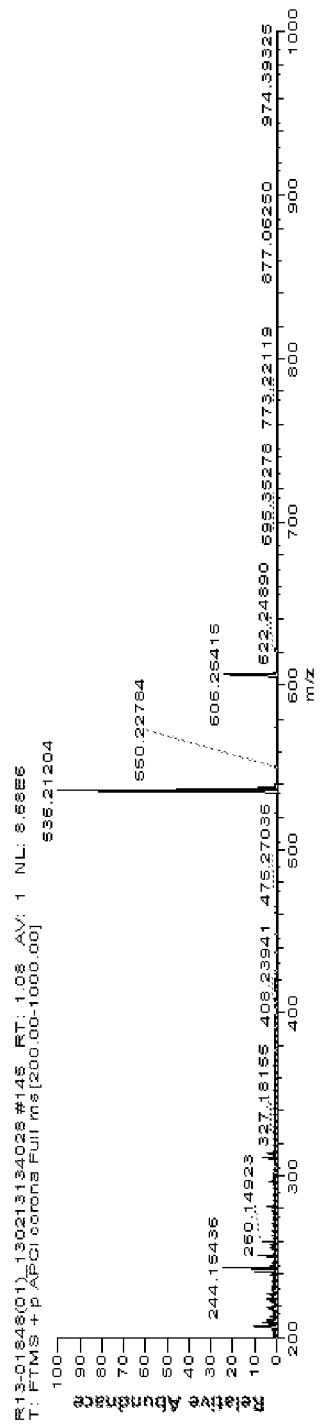
FIG. 9 shows the mass spectra of the compound of formula 2-48, synthesized in Preparation Example 7.

FIG. 9 shows the mass spectrum of the compound of formula 2-48, synthesized in Preparation Example 7.

Preparation Example 8

Preparation of Compound of Formula

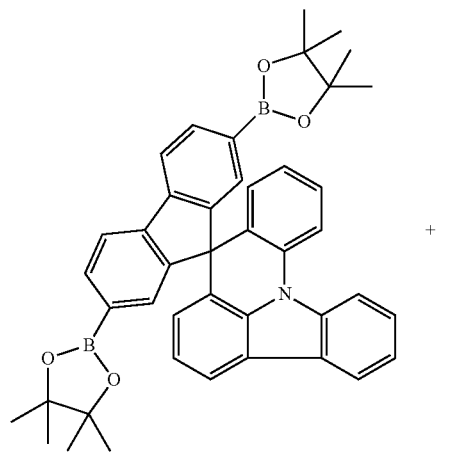

[Compound E]

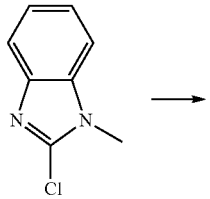

→

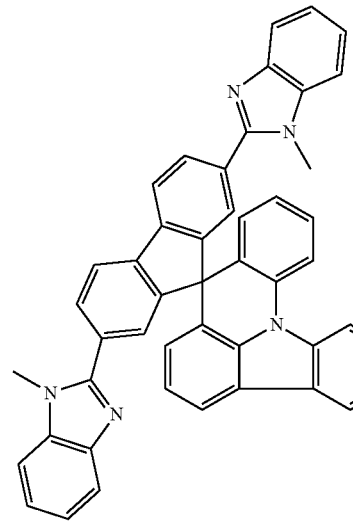

[Compound 2-53]

Compound E (11.4 g, 17.3 mmol) and 2-chloro-1-methyl-1H-benzoimidazole (6.4 g, 38.1 mmol) were completely dissolved in tetrahydrofuran (THF) (100 mL), and then a 2M aqueous solution of potassium carbonate (50 mL) was added thereto, and Pd(PPh$_3$)$_4$ (0.6 g, 3 mol %) was added thereto. Then, the mixture was stirred under reflux for 24 hours. The temperature of the mixture was lowered to room temperature, the aqueous layer was removed, and the organic layer was filtered. The resulting solid was purified by silica gel column chromatography, thereby obtaining the compound of formula 2-53 (4.4 g, 38%).

MS: [M+H]$^+$=666

Figure 10:
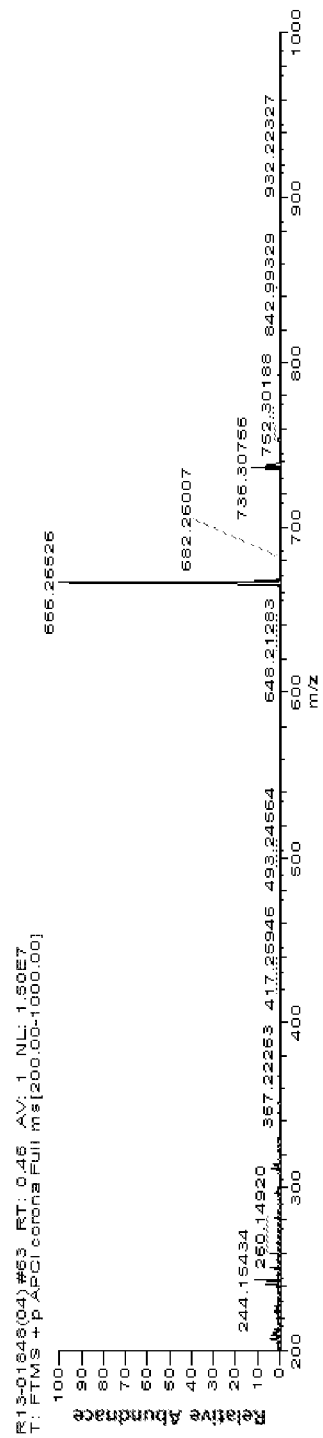
FIG. 10 shows the mass spectra of the compound of formula 202-53, synthesized in Preparation Example 8.

FIG. 10 shows the mass spectrum of the compound of formula 2-53, synthesized in Preparation Example 10.

Example 1

A glass substrate having ITO (indium tin oxide) coated thereon to a thickness of 500 Å was placed in distilled water containing a detergent dissolved therein, and was ultrasonically washed. Herein, the detergent was a product manufactured by Fischer Co., and the distilled water was distilled water filtered twice through a filter (Millipore Co.). After the ITO had been washed for 30 minutes, it was ultrasonically washed twice with distilled water for 10 minutes. After the completion of washing with distilled water, the substrate was ultrasonically washed with isopropyl alcohol, acetone and methanol solvents and was then dried, after which it was transported to a plasma cleaner. Then, the substrate was cleaned with oxygen plasma for 5 minutes, and then transferred to a vacuum evaporator.

On the transparent ITO electrode fabricated as described above, hexaazatriphenylene (HAT) was deposited to a thickness of 500 Å by a thermal vacuum deposition method to form a hole-injecting layer.

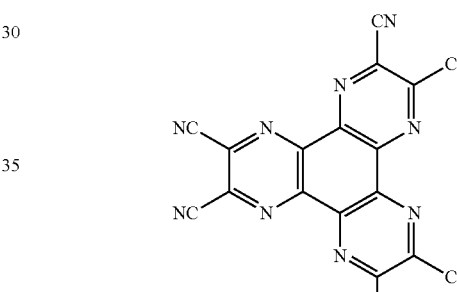

[HAT]

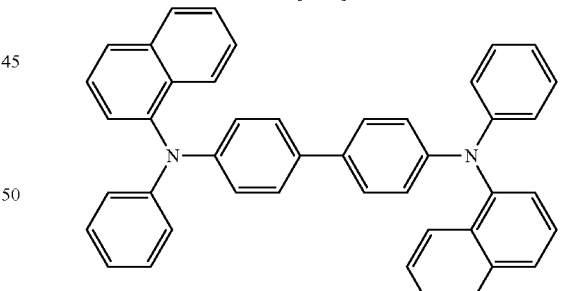

[NPB]

On the hole-injecting layer, 4-4'-bis[N-(1-naphthyl)-N-phenylamino]biphenyl (NPB) (250 Å) having the above formula, hexaazatriphenylene (HAT) (50 Å) and 4-4'-bis[N-(1-naphthyl)-N-phenylamino]biphenyl (NPB) (400 Å) were sequentially vacuum-deposited to form a hole-transporting layer.

On the hole-transporting layer, a 10:1 (w/w) mixture of the above-prepared compound of formula 2-1 and a dopant compound having the following formula GD was vacuum-deposited to a thickness of 300 Å to form a light-emitting layer:

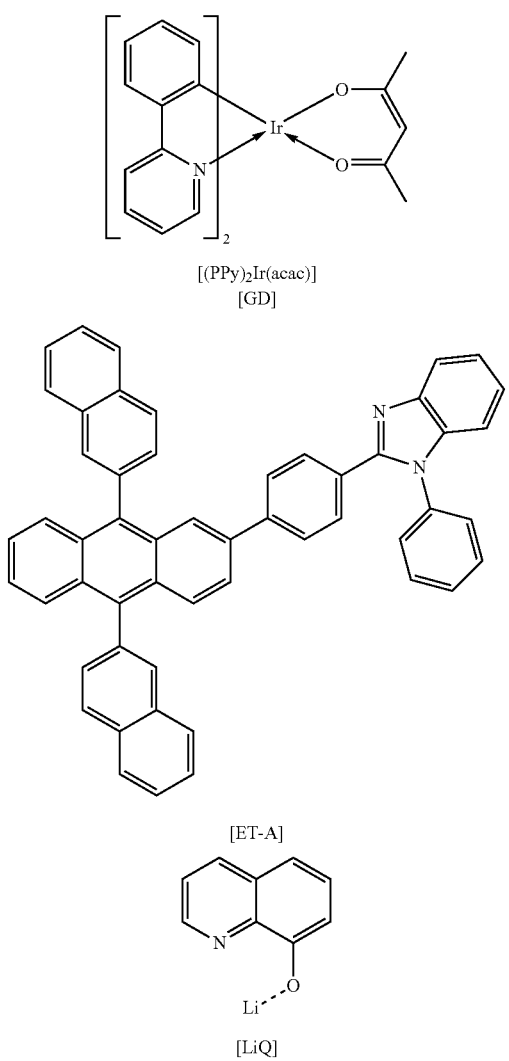

[(PPy)₂Ir(acac)]
[GD]

[ET-A]

[LiQ]

On the light-emitting layer, a 1:1 (w/w) mixture of the compound of formula ET-A and the lithium quinolate of formula LiQ was vacuum-deposited to a thickness of 300 Å to form an electron-injecting and electron-transporting layer.

On the electron-injecting and electron-transporting layer, lithium fluoride (LiF) and aluminum were sequentially deposited to thicknesses of 15 Å and 1,000 Å, respectively, to form a cathode.

In the above process for fabricating the organic light-emitting device, the deposition rate of the organic materials was maintained at 0.4-0.7 Å/sec, the deposition rates of lithium fluoride and aluminum for the cathode were maintained at 0.3 Å/sec and 2 Å/sec, respectively, and the strength of the vacuum during the deposition was maintained at $2 \times 10^{-7}$ to $5 \times 10^{-8}$ torr.

Example 2

An organic light-emitting device was fabricated in the same manner as described in Example 1, except that the compound of formula 2-3 was used instead of the compound of formula 2-1.

Example 3

An organic light-emitting device was fabricated in the same manner as described in Example 1, except that the compound of formula 2-16 was used instead of the compound of formula 2-1.

Example 4

An organic light-emitting device was fabricated in the same manner as described in Example 1, except that the compound of formula 2-29 was used instead of the compound of formula 2-1.

Example 5

An organic light-emitting device was fabricated in the same manner as described in Example 1, except that the compound of formula 2-35 was used instead of the compound of formula 2-1.

Example 6

An organic light-emitting device was fabricated in the same manner as described in Example 1, except that the compound of formula 2-46 was used instead of the compound of formula 2-1.

Example 7

An organic light-emitting device was fabricated in the same manner as described in Example 1, except that the compound of formula 2-48 was used instead of the compound of formula 2-1.

Example 8

An organic light-emitting device was fabricated in the same manner as described in Example 1, except that the compound of formula 2-53 was used instead of the compound of formula 2-1.

Comparative Example

An organic light-emitting device was fabricated in the same manner as described in Example 1, except that the compound of the following formula GH-A was used instead of the compound of formula 2-1.

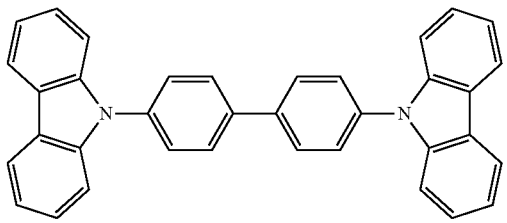

[GH-A]

When an electric current (10 mA/cm²) was applied to each of the organic light-emitting devices fabricated in the above Examples and Comparative Example, the results shown in Table 1 below were obtained.

TABLE 1

| | Compound | Voltage (V) | Efficiency (cd/A) |
|---|---|---|---|
| Example 1 | Formula 2-1 | 4.50 | 52.3 |
| Example 2 | Formula 2-3 | 4.80 | 47.1 |
| Example 3 | Formula 2-16 | 3.6 | 60.6 |
| Example 4 | Formula 2-29 | 4.55 | 56.8 |
| Example 5 | Formula 2-35 | 4.38 | 60.1 |
| Example 6 | Formula 2-46 | 4.50 | 52.3 |
| Example 7 | Formula 2-48 | 4.80 | 60.1 |
| Example 8 | Formula 2-53 | 4.50 | 52.3 |
| Comparative Example | GH-A | 6.12 | 15.26 |

As can be seen from the results in Table 1 above, the novel compound according to the present disclosure can be used as a material for a light-emitting layer in organic electronic devices, including organic light-emitting devices, and the organic electronic devices, including organic light-emitting devices, which comprise the novel compound, show excellent characteristics in terms of efficiency, driving voltage, stability and the like. Particularly, the novel compound can lower the driving voltage of the devices and increase the efficiency of the devices, thereby reducing the consumption of power.

DESCRIPTION OF REFERENCE NUMERALS USED IN THE FIGURES

1: Substrate
2: Anode
3 and 7: Light-emitting layer
4: Cathode
5: Hole-injecting layer
6: Hole-transporting layer
8: Electron-transporting layer

The invention claimed is:

1. A nitrogen-containing heterocyclic compound represented by the following formula 1:

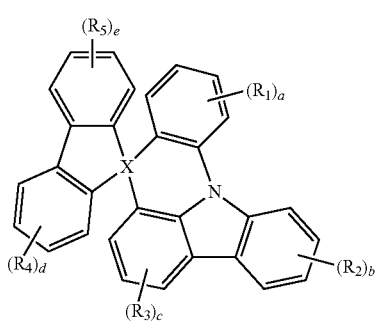

Formula 1 wherein
X is C or Si;
one or more of $R_1$ to $R_5$ are each independently represented by -L-A, wherein L is a direct bond or a divalent group containing one or more selected from the group consisting of a substituted or unsubstituted aromatic ring group and a substituted or unsubstituted heterocyclic group, and A is selected from the group consisting of a substituted or unsubstituted terphenyl group, a substituted or unsubstituted triphenylene group, a substituted or unsubstituted phenanthrene group, a substituted or unsubstituted phenanthroline group, a substituted or unsubstituted fluoranthene group, a substituted or unsubstituted fluorene group, a substituted or unsubstituted quinazoline group, a benzimidazole group substituted with an alkyl group, a substituted or unsubstituted dibenzothiophene group, and a substituted or unsubstituted dibenzofuran group;

the remainder of $R_1$ to $R_5$ are selected from the group consisting of hydrogen, deuterium, a halogen group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorene group, a substituted or unsubstituted carbazole group, and a substituted or unsubstituted heterocyclic group containing at least one heteroatom selected from N, O and S;

when one of A and $R_1$ to $R_5$ is a substituted or unsubstituted phenanthrene group, the phenanthrene group is represented by one of the following structures:

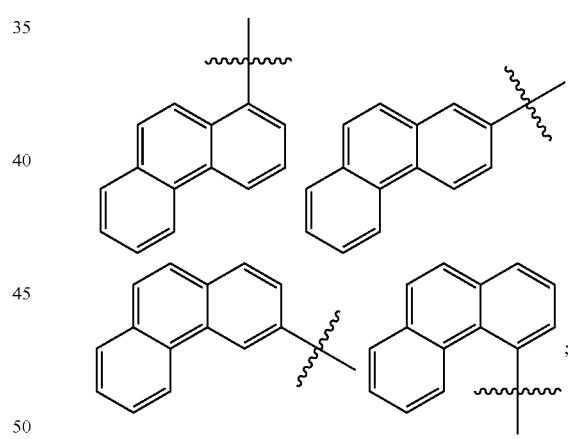

a, b, d and e are each independently an integer ranging from 1 to 4; and
c is an integer ranging from 1 to 3.

2. The nitrogen-containing heterocyclic compound of claim 1, wherein L in formula 1 is selected from the group consisting of a substituted or unsubstituted phenylene group, a substituted or unsubstituted biphenyl group, a substituted or unsubstituted naphthalene group, and a substituted or unsubstituted anthracene group.

3. The nitrogen-containing heterocyclic compound of claim 1, wherein L in formula 1 is a direct bond.

4. The nitrogen-containing heterocyclic compound of claim 1, wherein A is represented by any one of the following substituents 1-1, 1-2, 1-4 to 1-7, 1-9 to 1-12, and 1-15 to 1-23:

Substituent 1-1
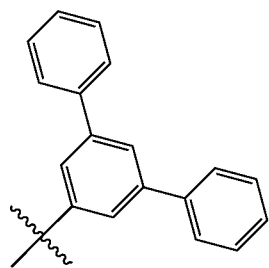
Substituent 1-2
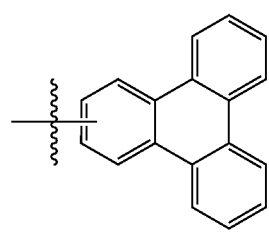
Substituent 1-4
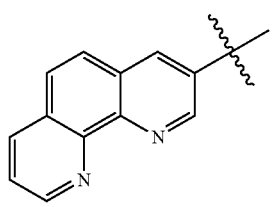
Substituent 1-5
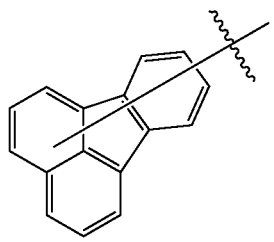
Substituent 1-6
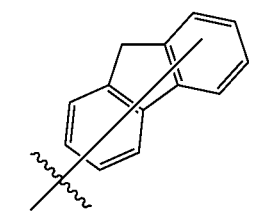
Substituent 1-7
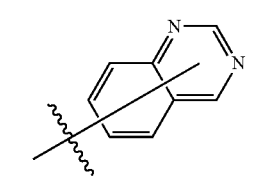
Substituent 1-9
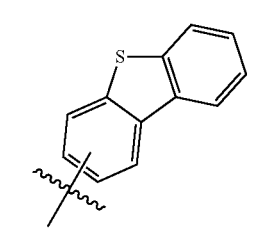
-continued
Substituent 1-10
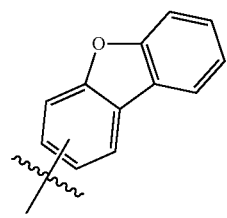
Substituent 1-11
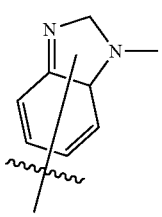
Substituent 1-12
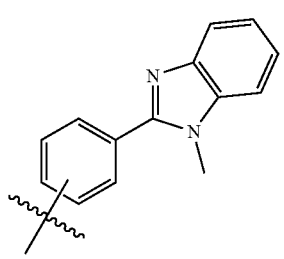
Substituent 1-15
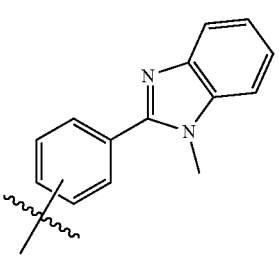
Substituent 1-16
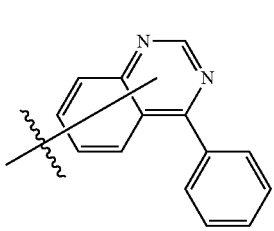
Substituent 1-17
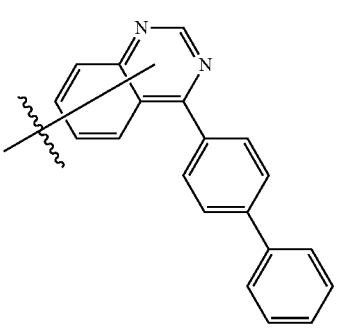

Substituent 1-18
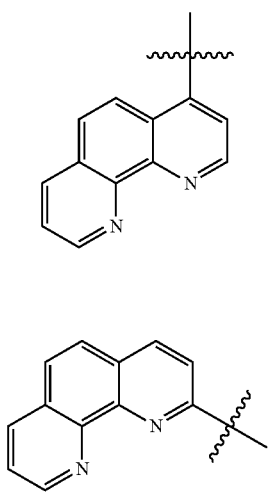
Substituent 1-19
Substituent 1-20
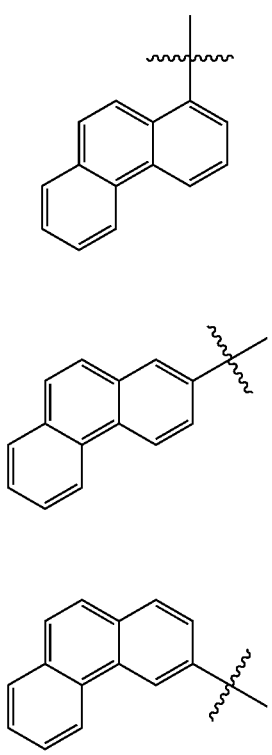
Substituent 1-21
Substituent 1-22
Substituent 1-23
5. The nitrogen-containing heterocyclic compound of claim 1, wherein the nitrogen-containing heterocyclic compound is represented by any one of the following formulas 2-1 to 2-10 and 2-14 to 2-68:
Formula 2-1
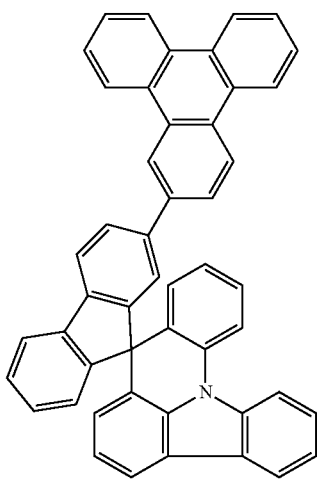
Formula 2-2
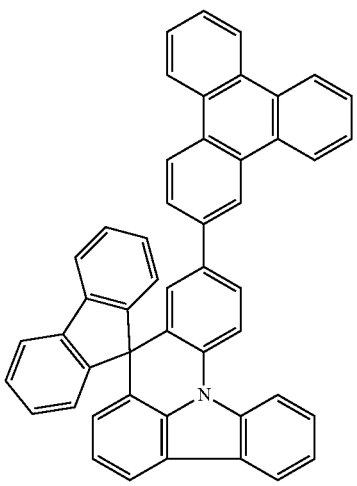
Formula 2-3
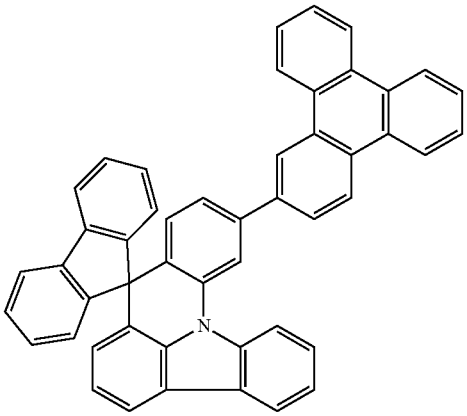

-continued
Formula 2-4
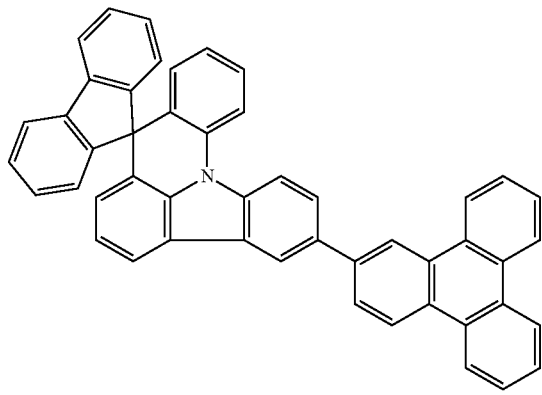
Formula 2-5
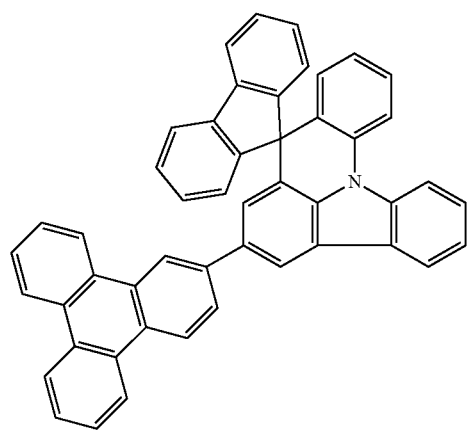
Formula 2-6
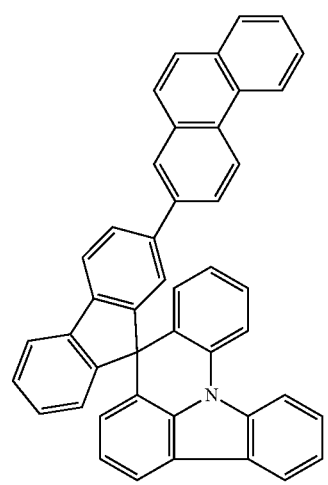
-continued
Formula 2-7
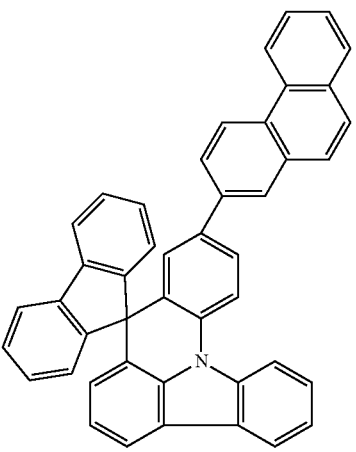
Formula 2-8
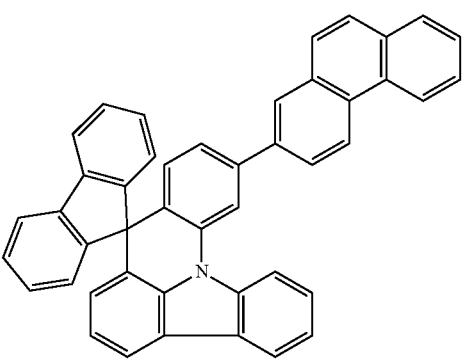
Formula 2-9
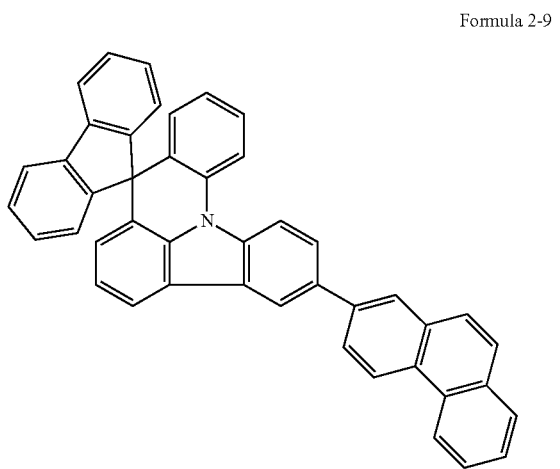

Formula 2-10
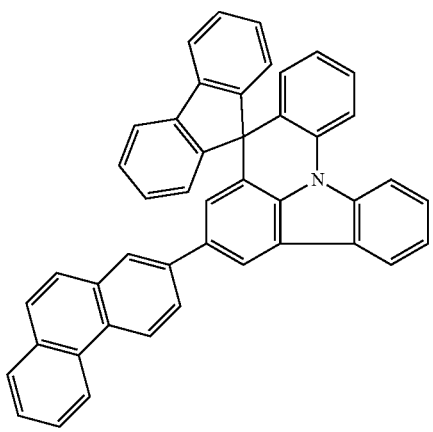
Formula 2-14
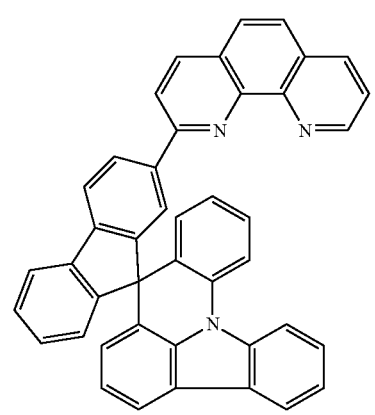
Formula 2-15
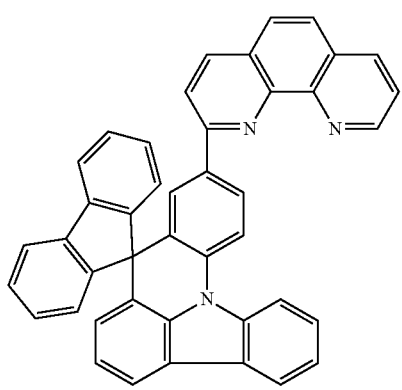
Formula 2-16
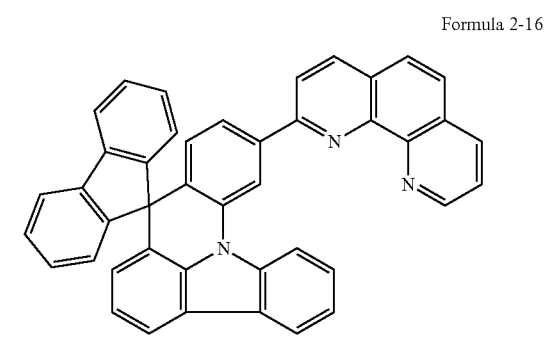
Formula 2-17
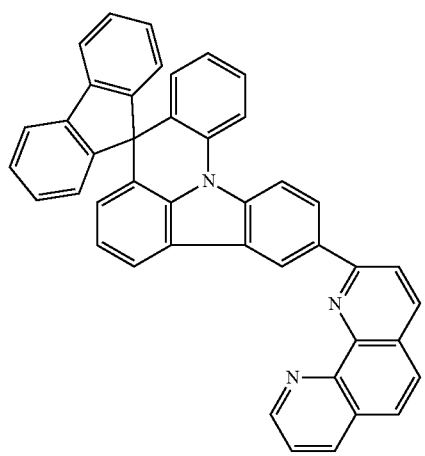
Formula 2-18
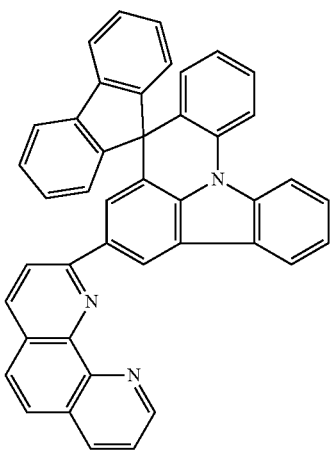
Formula 2-19
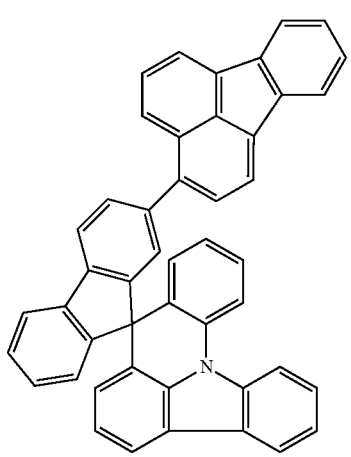

Formula 2-20
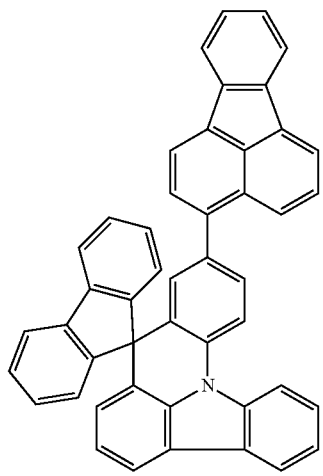
Formula 2-21
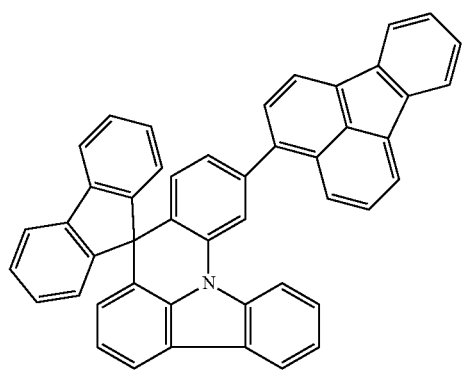
Formula 2-22
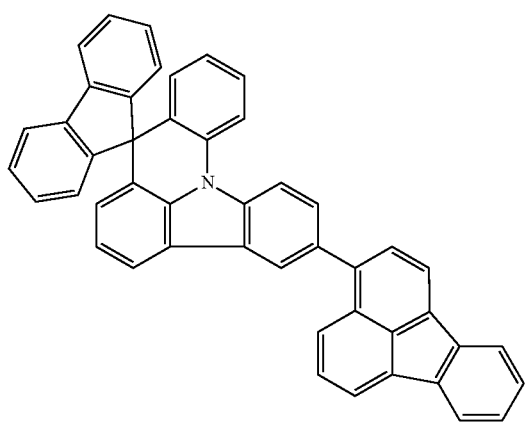
Formula 2-23
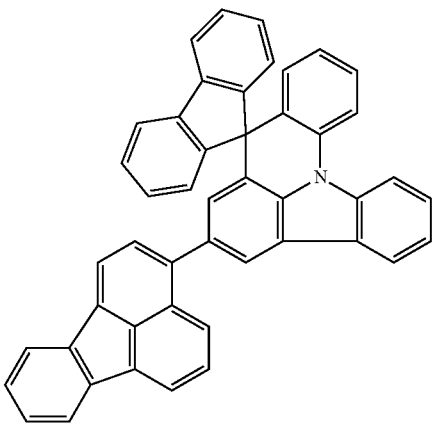
Formula 2-24
Formula 2-25
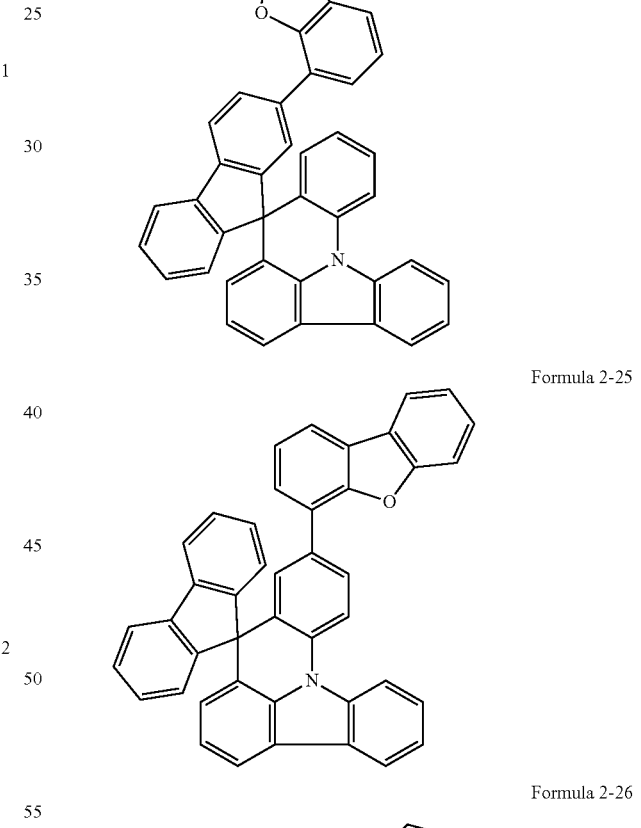
Formula 2-26
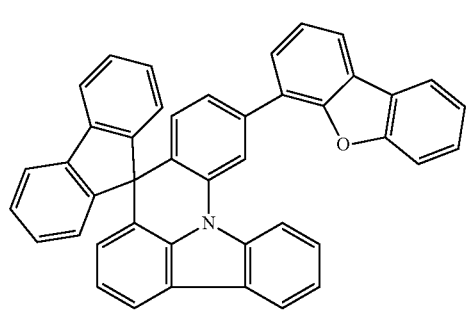

-continued
Formula 2-27
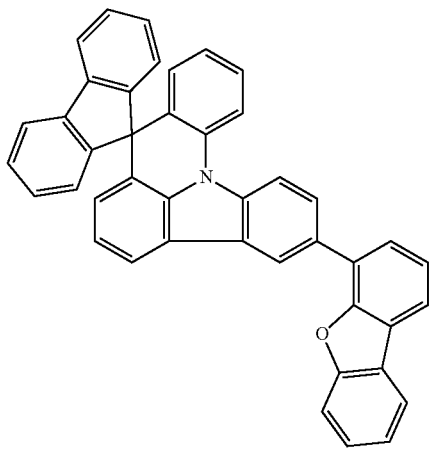
Formula 2-28
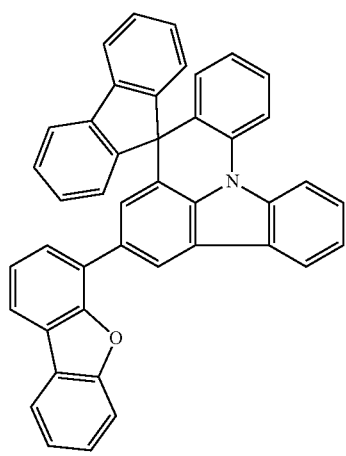
Formula 2-29
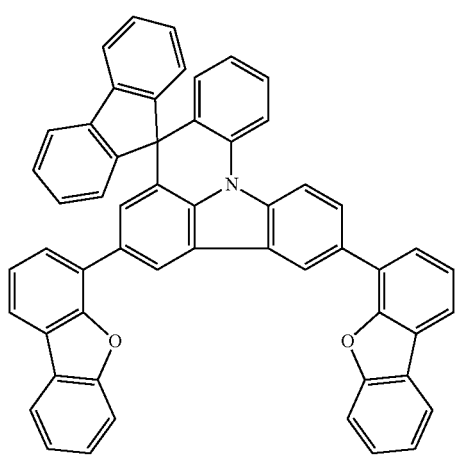
Formula 2-30
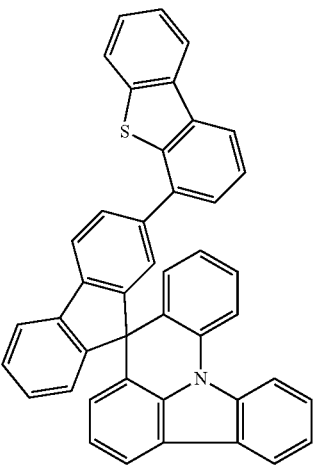
Formula 2-31
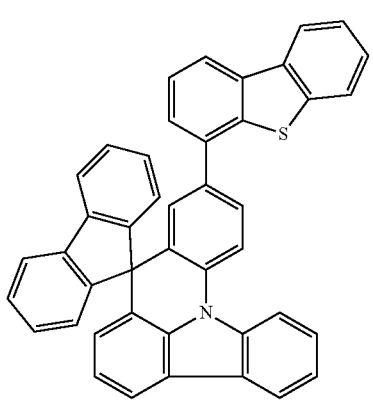
Formula 2-32
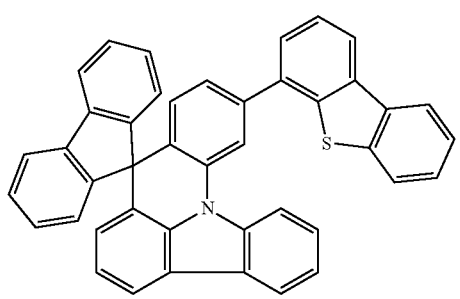
Formula 2-33
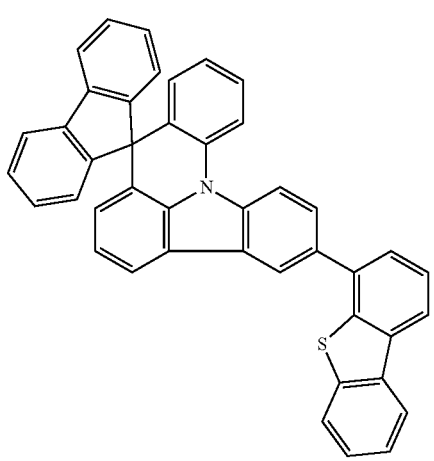

-continued
Formula 2-34
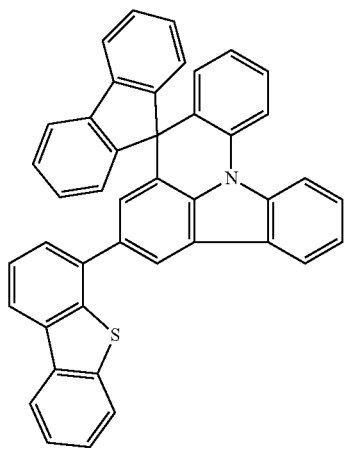
Formula 2-35
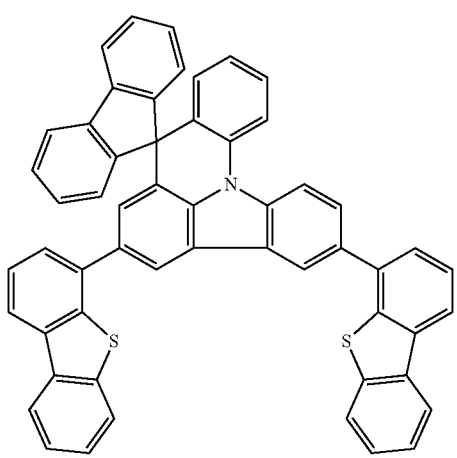
Formula 2-36
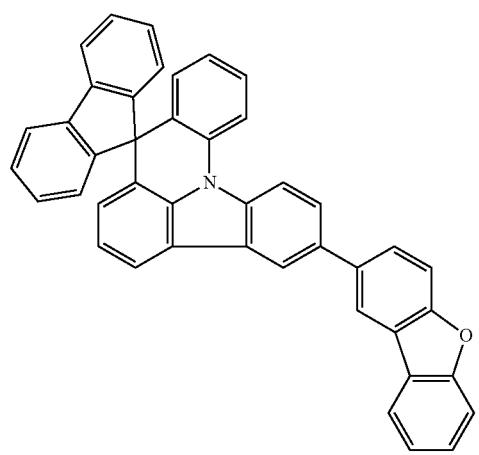
-continued
Formula 2-37
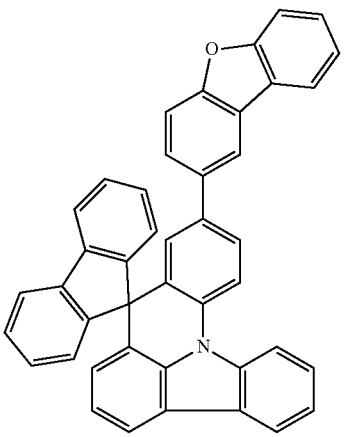
Formula 2-38
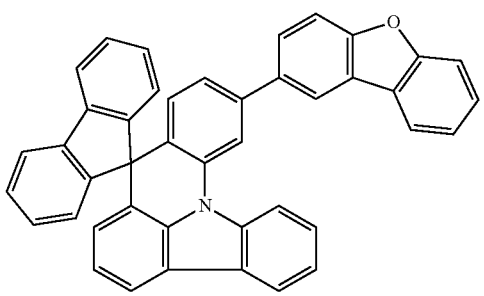
Formula 2-39
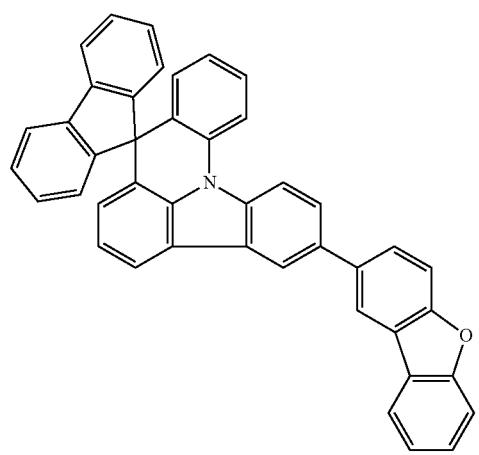

Formula 2-40
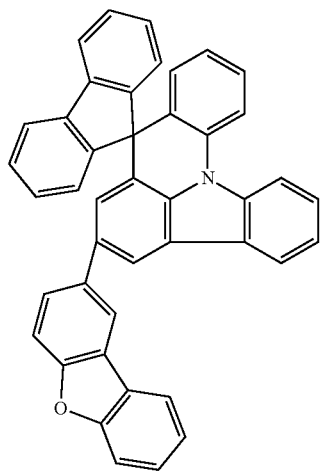
Formula 2-41
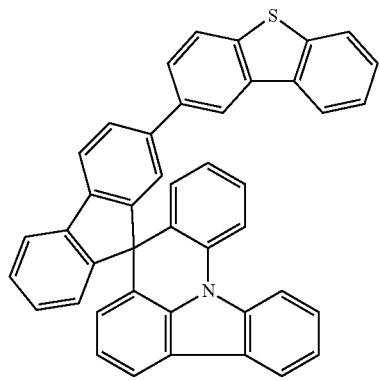
Formula 2-42
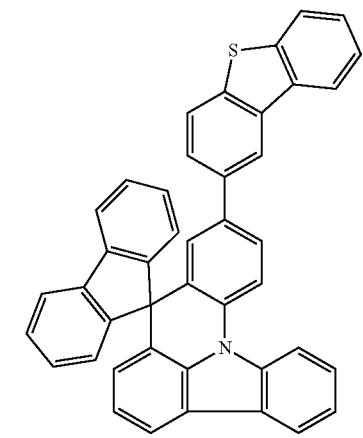
Formula 2-43
Formula 2-44
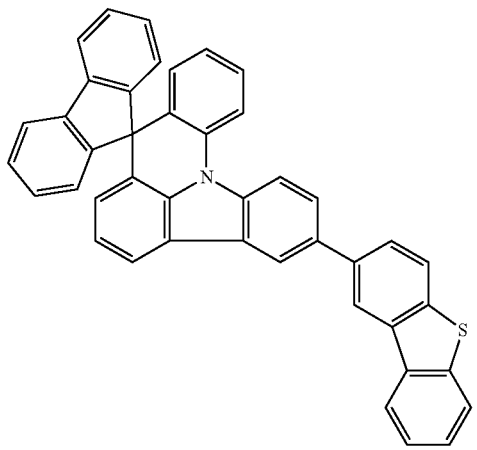
Formula 2-45
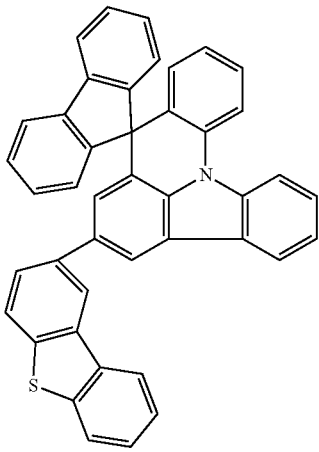
Formula 2-46
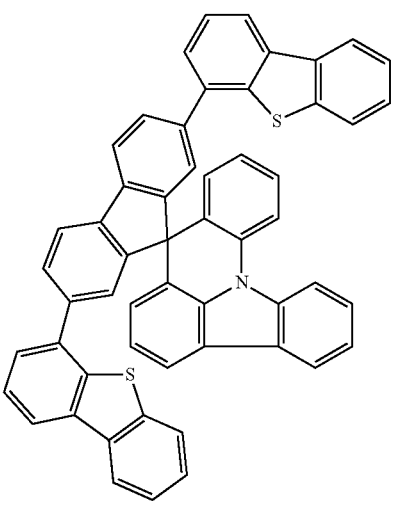

Formula 2-47
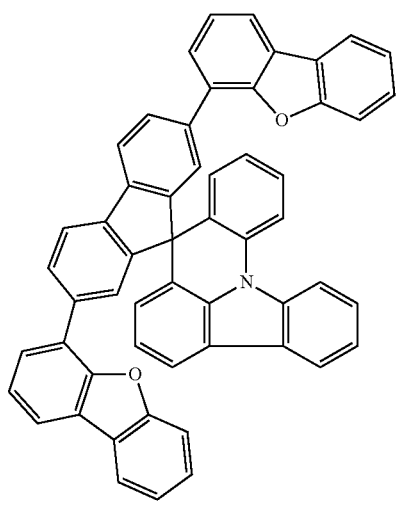
Formula 2-48
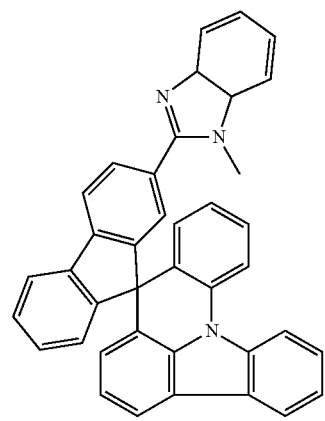
Formula 2-49
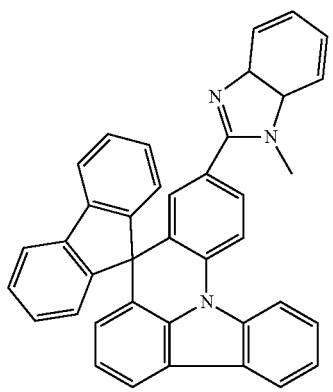
Formula 2-50
Formula 2-51
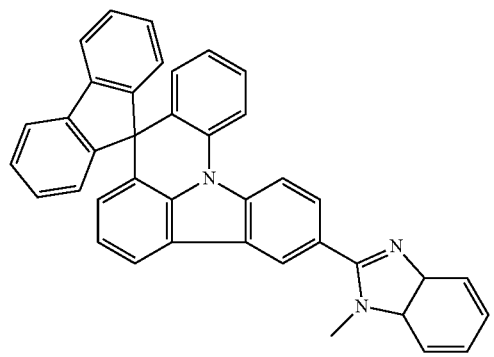
Formula 2-52
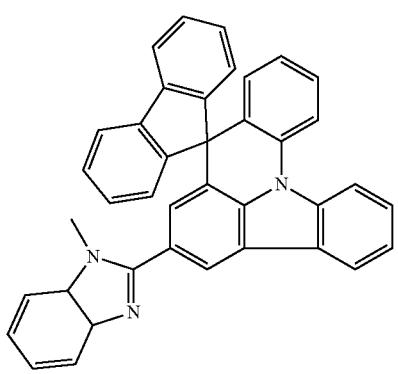
Formula 2-53
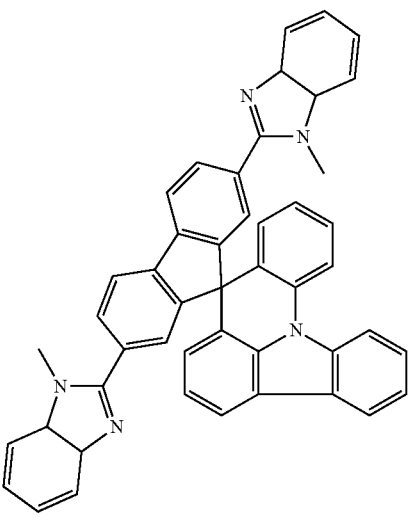

Formula 2-54
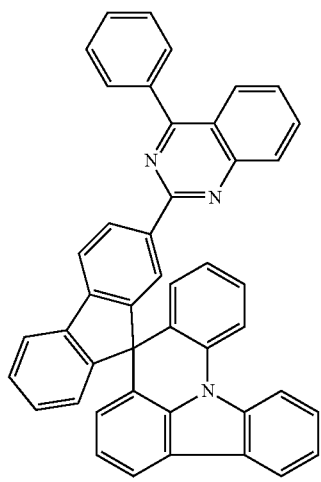
Formula 2-57
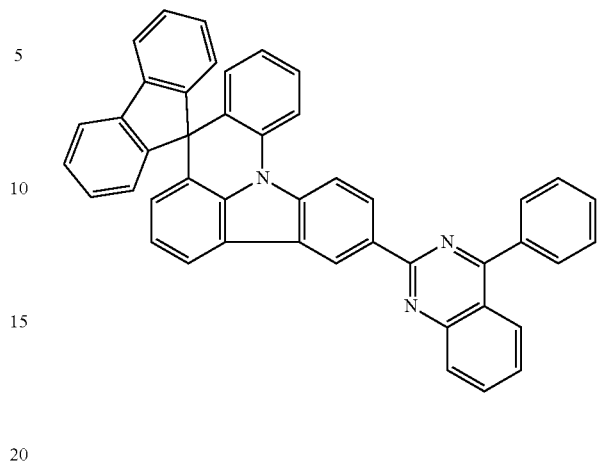
Formula 2-55
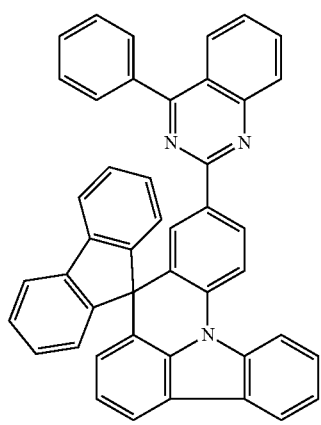
Formula 2-58
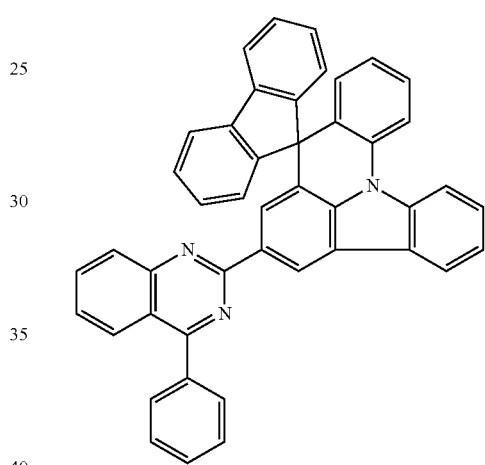
Formula 2-56
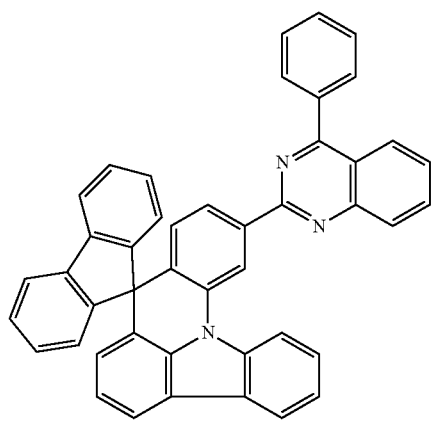
Formula 2-59
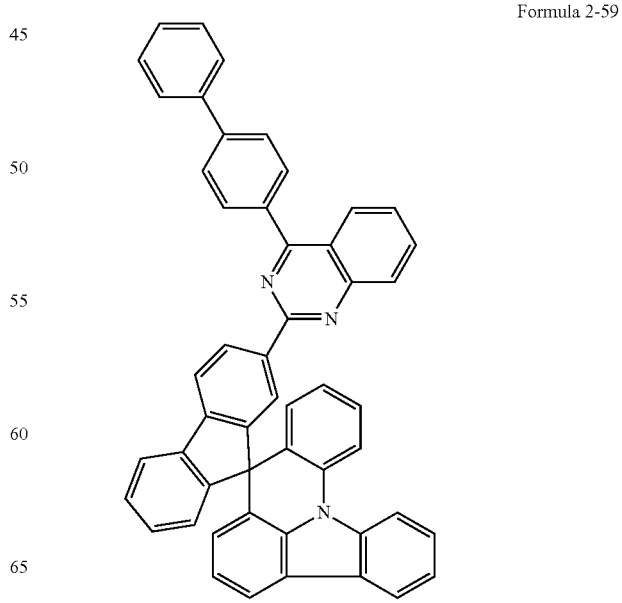

Formula 2-60
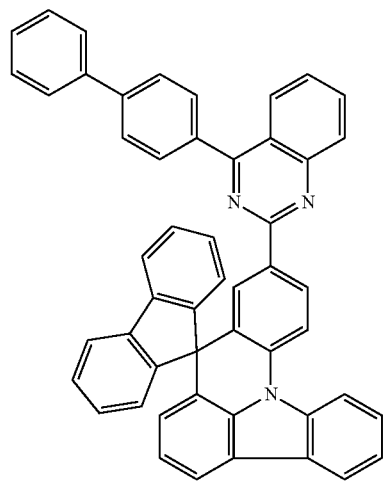
Formula 2-61
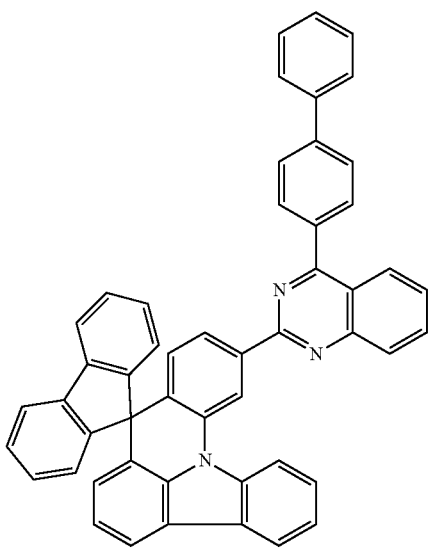
Formula 2-62
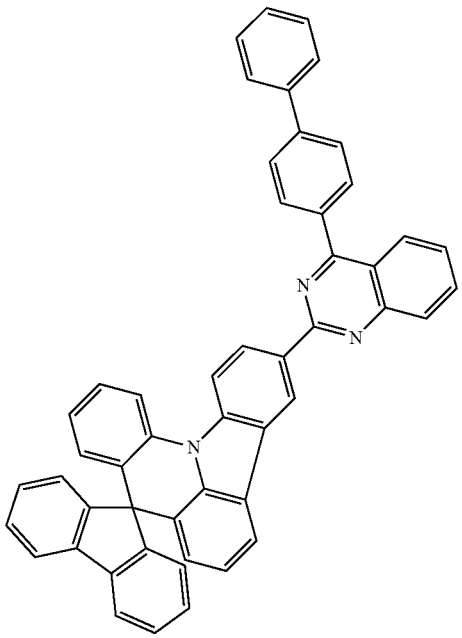
Formula 2-63
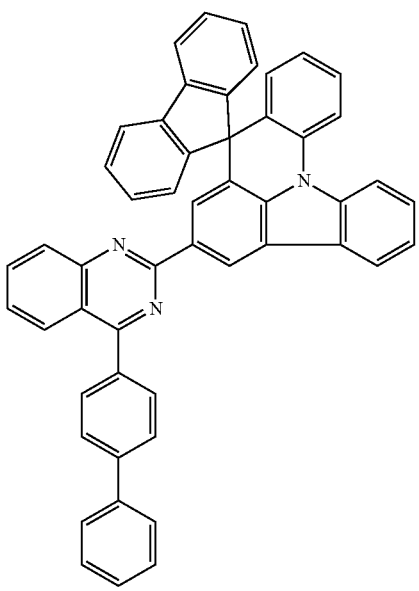

Formula 2-64
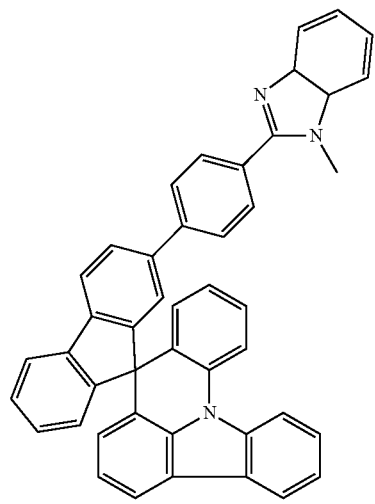

Formula 2-65
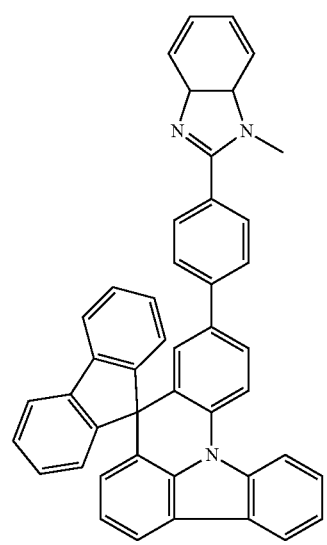

Formula 2-66
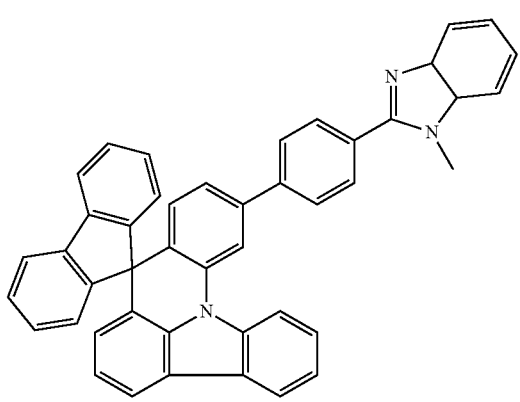

Formula 2-67
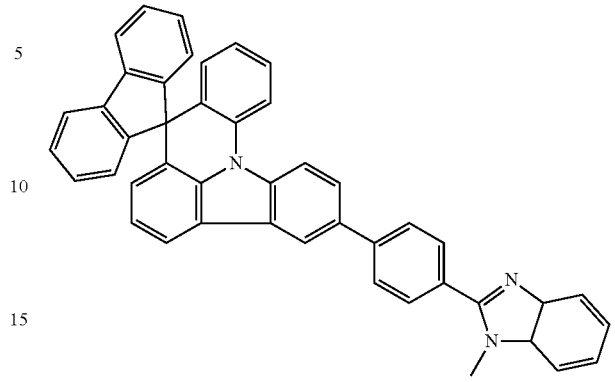

Formula 2-68
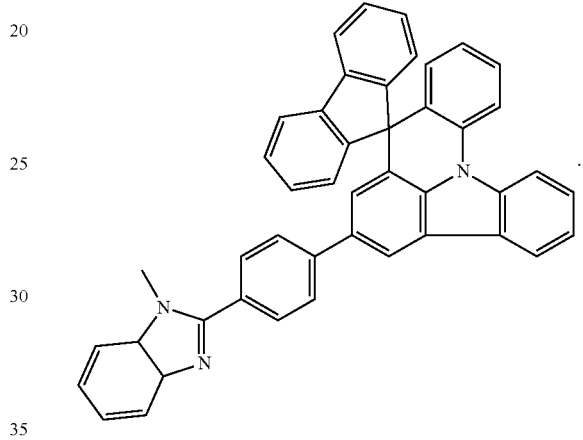

6. An organic electronic device comprising a first electrode, a second electrode opposite the first electrode, and one or more organic material layers interposed between the first electrode and the second electrode, wherein at least one of the organic material layers comprises the nitrogen-containing heterocyclic compound of claim 1.

7. The organic electronic device of claim 6, wherein the organic electronic device is selected from the group consisting of an organic solar cell, an organic light-emitting device, an organic transistor and an organic photo-conductor.

8. The organic electronic device of claim 6, wherein the organic electronic device is an organic light-emitting device comprising the first electrode, the second electrode opposite the first electrode, and the organic material layers, which are interposed between the first electrode and the second electrode and include a light-emitting layer, wherein at least one of the organic material layers comprises the nitrogen-containing heterocyclic compound.

9. The organic electronic device of claim 8, wherein the organic material layers further include one or more layer selected from the group consisting of a hole-transporting layer, a hole-blocking layer, an electrode-blocking layer, an electron-transporting layer, and an electron-injecting layer.

10. The organic electronic device of claim 8, wherein the organic material layer comprising the nitrogen-containing heterocyclic compound is an electron-transporting layer or a layer that performs both electron transport and light emission.

11. The organic electronic device of claim 6, wherein the organic electronic device is an organic solar cell comprising the first electrode, the second electrode opposite the first electrode, and the organic material layers, which are interposed between the first electrode and the second electrode and include a photoactive layer, wherein at least one of the organic material layers comprises the nitrogen-containing heterocyclic compound.

12. The organic electronic device of claim 11, wherein the organic material layer comprising the nitrogen-containing heterocyclic compound further comprises one or more layer selected from the group consisting of an electron donor and an electron acceptor.

13. The organic electronic device of claim 11, wherein the organic material layer comprising the nitrogen-containing heterocyclic compound is the photoactive layer having one more layer selected from the group consisting of an electron donor and an electron acceptor.

14. The organic electronic device of claim 6, wherein the organic electronic device is an organic transistor comprising a source, a drain, a gate and one or more organic material layers, wherein at least one of the organic material layers comprises the nitrogen-containing heterocyclic compound.

15. The organic electronic device of claim 6, wherein the organic electronic device is an organic photo-conductor comprising the first electrode, the second electrode opposite the first electrode, one or more organic material layers, which are disposed between the first electrode and the second electrode and include an organic photosensitive layer, wherein at least one of the organic material layers comprises the nitrogen-containing heterocyclic compound.

16. A method for fabricating an organic electronic device, the method comprising the steps of:

providing a substrate;

forming a first electrode on the substrate;

forming, over the first electrode, an organic material layer comprising the nitrogen-containing heterocyclic compound of claim 1; and forming a second electrode over the organic material layer.

* * * * *